(12) United States Patent
Berman et al.

(10) Patent No.: US 7,125,394 B2
(45) Date of Patent: Oct. 24, 2006

(54) APPLICATOR FOR DISPENSING A MEDICINAL SUBSTANCE

(75) Inventors: Irwin R. Berman, Saint Simons Island, GA (US); Richard D. Gillespie, Athens, TX (US); Gervasio Salgado, Marbella (ES)

(73) Assignee: Syringe, LLC, Saint Simons Island, GA (US)

( * ) Notice: Subject to any disclaimer, the term of this patent is extended or adjusted under 35 U.S.C. 154(b) by 0 days.

(21) Appl. No.: 10/446,739

(22) Filed: May 29, 2003

(65) Prior Publication Data

US 2004/0015120 A1 Jan. 22, 2004

Related U.S. Application Data

(63) Continuation-in-part of application No. 10/160,166, filed on Jun. 4, 2002.

(51) Int. Cl.
*A61M 31/00* (2006.01)
*A61F 13/20* (2006.01)

(52) U.S. Cl. .............................. 604/60; 604/15; 604/57

(58) Field of Classification Search ............ 604/11–18, 604/47, 48, 36–42, 57–64, 289, 310, 311, 604/290
See application file for complete search history.

(56) References Cited

U.S. PATENT DOCUMENTS

| | | | |
|---|---|---|---|
| 694,971 A | 3/1902 | Kistler | |
| 1,567,009 A * | 12/1925 | Sterritt | 604/182 |
| 1,818,670 A | 8/1931 | Bixler | |
| 2,474,496 A | 6/1949 | Rayman | |
| 2,631,586 A * | 3/1953 | Reilly | 604/104 |
| 2,695,023 A | 11/1954 | Brown | |
| 2,764,981 A | 10/1956 | Helmer et al. | |
| 2,875,761 A | 3/1959 | Helmer et al. | |
| 3,076,455 A | 2/1963 | McConnaughey et al. | |
| 3,109,427 A * | 11/1963 | Davidson | 604/212 |
| 3,429,642 A | 2/1969 | Underwood | |
| 3,536,411 A * | 10/1970 | Eisert | 401/176 |
| 3,894,539 A | 7/1975 | Tallent | |
| 3,934,586 A | 1/1976 | Easton et al. | |

(Continued)

FOREIGN PATENT DOCUMENTS

DE   3513646 A1   10/1986

(Continued)

OTHER PUBLICATIONS

Salgado et al., "Headaches in the Treatment of Anal Fissures," Diseases of the Colon & Rectum, 1999, vol. 42, No. 8, p. 1106.

(Continued)

*Primary Examiner*—Kevin C. Sirmons
*Assistant Examiner*—Benjamin Huh
(74) *Attorney, Agent, or Firm*—J. Bruce Hoofnagle

(57) ABSTRACT

A device 560, for administering multiple single doses of a medicated cream, includes a cartridge 562 having a barrel 564 for containing the cream, a plunger 608 for moving the cream from within the cartridge, and a stem 610 for moving the plunger within the cartridge. A carrier 612 is formed with a cartridge-receiving nest 712 for receiving the barrel 564. A plurality of spaced, transaxial grooves 726, 728, 730 and 732 are formed in the carrier 612 for receiving a flange 572 of the cartridge 562 during the dispensing of multiple, successive, single doses of the cream. The carrier 612 is formed with a pair of resilient ears 750 and 752 and a passage 738 for removably retaining the stem 610 with the carrier while allowing axial movement of the stem.

10 Claims, 9 Drawing Sheets

U.S. PATENT DOCUMENTS

| | | | |
|---|---|---|---|
| 3,965,901 A * | 6/1976 | Penny et al. ................ 604/119 |
| 4,017,007 A | 4/1977 | Riccio |
| 4,361,150 A * | 11/1982 | Voss ............................ 604/15 |
| 4,466,426 A | 8/1984 | Blackman |
| 4,560,376 A | 12/1985 | Cannon |
| 4,585,445 A | 4/1986 | Hadtke |
| 4,654,035 A | 3/1987 | Ando |
| 4,659,327 A | 4/1987 | Bennett et al. |
| 4,874,385 A | 10/1989 | Moran et al. |
| 4,997,423 A | 3/1991 | Okuda et al. |
| 5,048,684 A | 9/1991 | Scott |
| 5,217,436 A | 6/1993 | Farkas |
| 5,217,442 A | 6/1993 | Davis |
| 5,219,448 A | 6/1993 | Hackmann |
| 5,279,586 A | 1/1994 | Balkwill |
| 5,431,680 A | 7/1995 | Jones |
| 5,433,352 A | 7/1995 | Ronvig |
| 5,451,214 A | 9/1995 | Hajishoreh |
| 5,478,321 A | 12/1995 | Kimber |
| 5,531,703 A | 7/1996 | Skwarek et al. |
| 5,599,314 A | 2/1997 | Neill |
| 5,609,581 A * | 3/1997 | Fletcher et al. ............. 604/212 |
| 5,688,252 A | 11/1997 | Matsuda et al. |
| 5,695,481 A | 12/1997 | Heinzelman et al. |
| 5,728,076 A | 3/1998 | Loos et al. |
| 5,769,825 A | 6/1998 | Lynn |
| 5,830,547 A | 11/1998 | MacKenzie et al. |
| 6,063,062 A | 5/2000 | Paradis |
| 6,090,082 A | 7/2000 | King et al. |
| 6,162,202 A | 12/2000 | Sicurelli et al. |
| 6,168,576 B1 | 1/2001 | Reynolds |
| 6,241,709 B1 | 6/2001 | Bechtold et al. |
| 6,258,063 B1 * | 7/2001 | Haar et al. .................. 604/141 |
| 6,258,068 B1 | 7/2001 | Kirchhofer et al. |
| 6,378,218 B1 * | 4/2002 | Sigwart et al. ............... 30/363 |
| 6,589,216 B1 * | 7/2003 | Abbott et al. ............... 604/279 |

FOREIGN PATENT DOCUMENTS

| | | |
|---|---|---|
| DE | 3720346 A1 | 12/1988 |
| EP | 0761173 A2 | 3/1997 |
| EP | 0761173 A3 | 7/1997 |

OTHER PUBLICATIONS

Pamphlet by Ferndale Laboratories Inc. "Introducing Applicoater™" Apr. 2004.

UK Patent Office Examination Report Under Section 18(3); UK Appl. No. GB0428458.4; Date: Jun. 24, 2005.

UK Patent Office Examination Report Under Section 18(3); UK Appl. No. GB0428458.4; Date: Nov. 21, 2005.

UK Patent Office Examination Report Under Section 18(3); UK Appl. No. GB0428458.4; Date: Apr. 11, 2006.

* cited by examiner

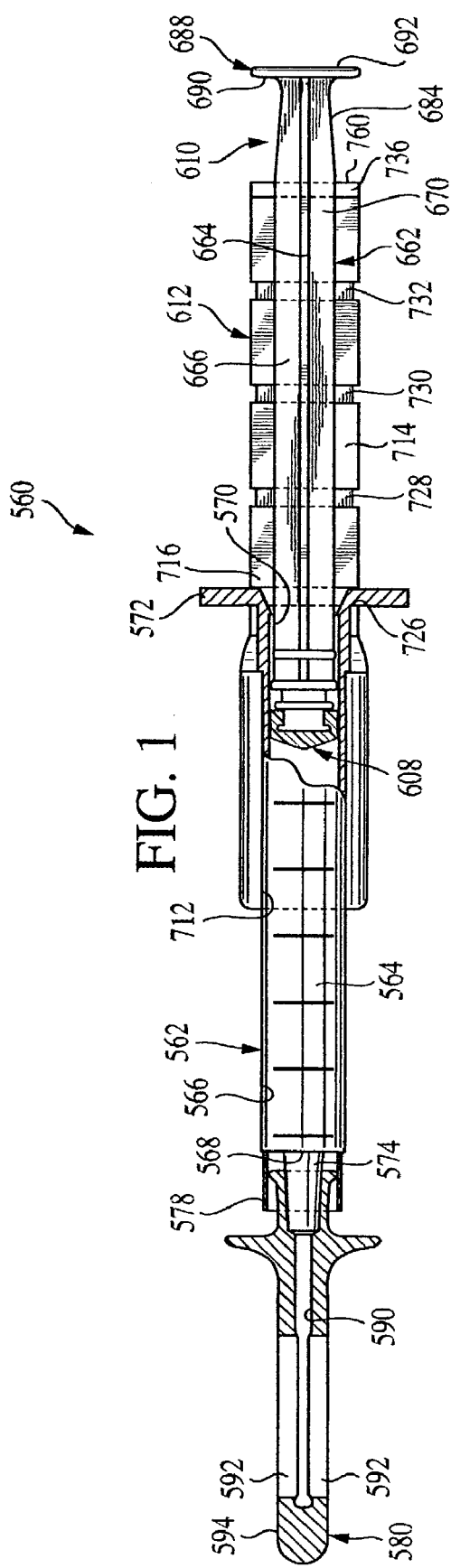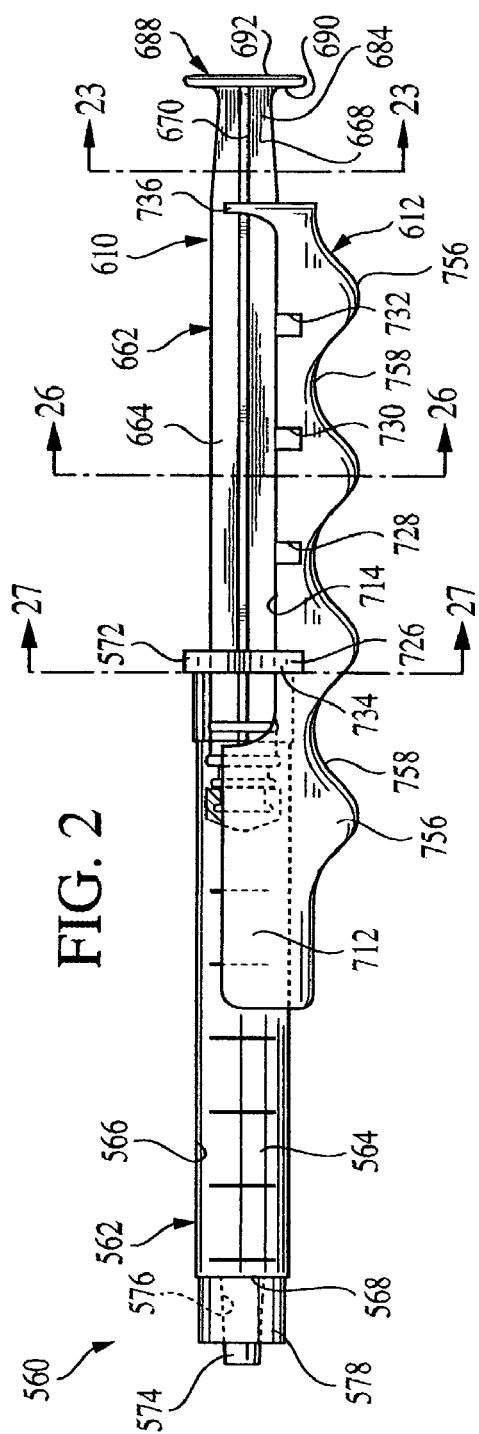

APPLICATOR FOR DISPENSING A MEDICINAL SUBSTANCE

This application is a continuation-in-part of co-pending application Ser. No. 10/160,166, filed Jun. 4, 2002, which is incorporated herein by reference thereto.

BACKGROUND OF THE INVENTION

This invention relates to an applicator for dispensing a medicinal substance, and particularly relates to an applicator for providing a delivery passage for a medicinal substance.

Various medical conditions, which are located within the vaginal and/or anal openings of the human anatomy, can be treated with medicinal creams and other substances of similar consistency. Frequently, such creams are prescribed by physicians, and are to be applied in measured dosages over a period of time. Because of the necessity for frequent applications of the cream to the affected locations, it is beneficial and economical for the patient to self-administer the measured dosage applications.

However, the act of administering the medicinal cream in such areas, frequently places the patient in awkward physical positions, which require a level of dexterity not inherent in some patients. Under these conditions, imprecise amounts of the cream could be administered undesirably.

In the past, several devices have been developed for storing multiple doses of the medicinal substances within a barrel of a syringe or a cartridge, to facilitate the successive application of time-spaced doses over a period of time. Such devices also include a plunger within the barrel, and a stem for engaging the plunger and urging the cream in successive doses from within the barrel, and through a dispensing means such as an applicator.

Cleanliness of such devices is unpredictable, during dispensing and during storage and transporting thereof. Thus, there is a need for a multiple-dose delivery device which can be easily cleaned while retaining the cream within the barrel, and also during storage and transporting of the device between the time-spaced administering of successive doses of the cream. Also, there is a need for a multiple-dose delivery device which can be dismantled easily for effective cleaning, and for storage and portability.

Devices developed in the past facilitate the dispensing of the cream generally within the vaginal and/or anal openings, but tend not provide structure which focuses the cream directly onto the critical areas for a most effective treatment.

Thus, there is a need for a multiple-dose delivery device, and an applicator thereof, which focuses the cream directly onto the critical areas to be treated.

SUMMARY OF THE INVENTION

It is, therefore, an object of this invention to provide a focused dosimetry device, which can be easily cleaned while retaining the cream in the cartridge barrel.

Another object of this invention is to provide a focused dosimetry device which can be easily dismantled for effective cleaning, storage and portability.

An additional object of this invention is to provide a focused dosimetry device with an applicator, and an applicator independently of the device, which focuses the dispensed cream directly onto the critical areas to be treated.

With these and other objects in mind, this invention contemplates a focused dosimetry device which includes a cartridge formed with a barrel having a passage formed through the barrel along an axis thereof between a proximal end of the barrel and an axially spaced distal end of the barrel. A plunger is locatable and movable within the passage of the barrel, and is formed with a proximal surface. A stem has an integrally formed distal surface mounted for movement independently of the plunger through the proximal end of, and into the passage of, the barrel for interfacing engagement with the proximal surface of the plunger to facilitate movement of the plunger within the barrel.

This invention also contemplates a carrier and stem assembly for a focused dosimetry device, which includes a stem having a distal end and a proximal end spaced from the distal end thereof. The stem is formed with an intermediate section along an axis of the stem between the distal end and the proximal end thereof. The intermediate section of the stem is formed with a prescribed cross section. The device also includes a carrier. Means are formed on the carrier for removably retaining the intermediate section of the stem with the carrier, and means are formed on the carrier for allowing the intermediate section of the stem to be moved along the axis of the stem relative to the means for removably retaining the intermediate section.

In addition, this invention contemplates a focused dosimetry device which includes a cartridge formed with a barrel having a passage through the barrel between a proximal end of the barrel and an axially spaced distal end of the barrel. The barrel has an exterior shape of a prescribed configuration, with a plunger locatable and movable within the passage of the barrel. A stem has a distal end positionable through the proximal end of, and to a position within the passage of, the barrel to facilitate movement of the plunger within the barrel. The stem is formed with a proximal end spaced from the distal end thereof, and is formed with an intermediate section along an axis of the stem between the distal end and the proximal end thereof. The intermediate section of the stem is formed with a prescribed cross section. A carrier of the device is formed with a barrel-receiving nest. Means are provided for retaining the barrel within the barrel-receiving nest. Means are also provided for removably retaining the intermediate section of the stem with the carrier. Further, means are provided for allowing the intermediate section of the stem to be moved along the axis of the stem relative to the means for removably retaining the intermediate section.

Further, this invention contemplates a focused dosimetry device, which includes an applicator for dispensing a substance therethrough, which includes a body formed with an axial entry passage extending from a proximal end of the body toward a distal end of the body and to a distal end of the passage. The axial entry passage is formed with a prescribed diameter, and the body is formed with an axial delivery passage having a proximal end in communication with the distal end of the axial entry passage. The axial delivery passage of the applicator extends from the proximal end of the axial delivery passage body toward the distal end of the body and to a closed distal end of the axial delivery passage, and is formed with a diameter which is less than the prescribed diameter. At least one elongated slot is formed through the body in communication with the axial delivery passage and an exterior of the body, and is formed with interfacing side walls which extend from a proximal end to a distal end of the slot.

Still further, this invention contemplates an applicator for dispensing a substance therethrough, which includes a body formed with a prescribed external diameter, and with an axial delivery passage extending from a proximal end of the body toward a distal end of the body and to a distal end of the passage. The axial delivery passage is formed with a diameter which is less than the prescribed diameter.

Also, this invention contemplates an applicator for dispensing a substance therethrough, which includes a body formed with an axis and an external surface between a proximal end and a distal end thereof. A flange extends radially outward from the external surface of the body to an outer edge surface of the flange, and has a proximal surface facing in a direction toward the proximal end of the body and a distal surface facing in a direction toward the distal end of the body. The distal surface of the flange is formed by a flat portion, which extends from the outer edge of the flange, radially inward toward the axis of the body and toward the distal end of the body, to an inboard edge of the flat portion spaced radially outward from the external surface of the body. The distal surface of the flange is formed with a concave portion which extends from the inboard edge of the flat surface toward the distal end, and to the external surface, of the body.

Additionally, this invention contemplates a cartridge and applicator assembly for a focused dosimetry device, which includes a cartridge formed with a barrel having a distal end, and an axial passage having a prescribed diameter. An applicator is formed with a body having a proximal end, and an axial delivery passage having a uniform diameter which is less than the prescribed diameter between a proximal end and a distal end thereof. Means are provided for attaching the proximal end of the applicator to the distal end of the barrel such that the axial passage of the barrel is in communication with the axial delivery passage of the applicator.

Also, this invention contemplates a method of dispensing successively two doses of a substance from a distal end of a barrel containing the substance, which includes the steps of placing the barrel at a first prescribed location, placing a distal end of a stem through a proximal end of the barrel and into engagement with a plunger within the barrel, moving the stem toward the distal end of the barrel to dispense the substance from the distal end of the barrel, moving a surface of the stem into engagement with a stop surface after the stem has travelled through a prescribed stem-travel distance whereby a given amount of the substance has been dispensed from the distal end of the barrel; moving the barrel and the stem to a second prescribed location in a direction away from the stop surface whereby the surface of the stem is spaced from the stop surface by a distance equal to the prescribed stem-travel distance; moving the stem toward the distal end of the barrel to dispense the substance from the distal end of the barrel; and moving the surface of the stem into engagement with the stop surface after the stem has travelled through the prescribed stem-travel distance whereby an amount of the substance equal to the given amount has been dispensed from the distal end of the barrel.

Other objects, features and advantages of the present invention will become more fully apparent from the following detailed description of the preferred embodiment, the appended claims and the accompanying drawings.

BRIEF DESCRIPTION OF THE DRAWINGS

In the accompanying drawings:

FIG. 1 is a partially-sectioned top view showing a focused dosimetry device, including a cartridge nested in a carrier having spaced grooves for receiving a flange of the cartridge, and a stem nested in the carrier and, together with an applicator, in assembly with the cartridge, in accordance with certain principles of the invention;

FIG. 2 is a side view showing the cartridge and the stem nested in the carrier, and finger-locating grooves on the carrier, of the focused dosimetry device of FIG. 1, with the stem in assembly with the cartridge, in accordance with certain principles of the invention;

FIG. 8 is a partial sectional view showing a third embodiment of a thumb rest of the stem of FIG. 1, in accordance with certain principles of the invention;

DETAILED DESCRIPTION OF THE INVENTION

Figure 3:
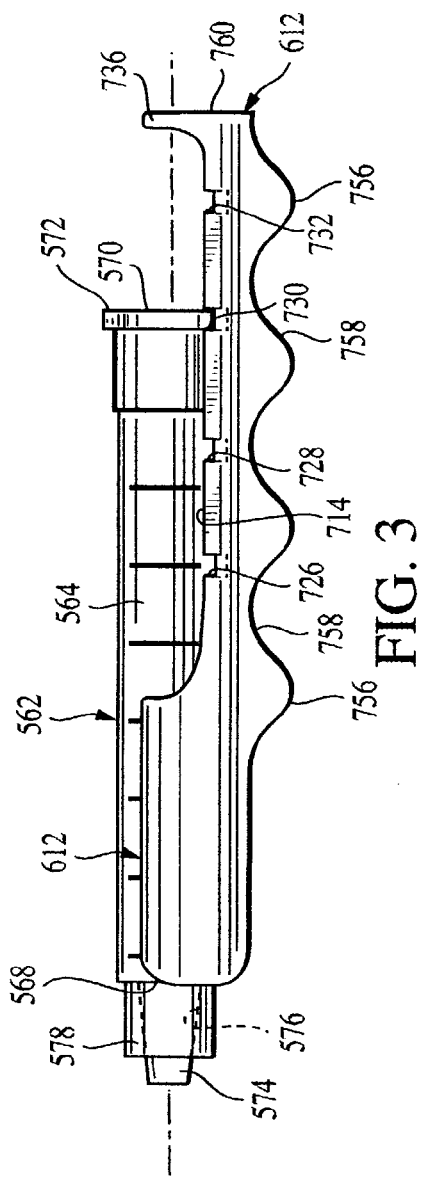
FIG. 3 is a side view showing the assembly of the cartridge and the carrier of FIG. 1, in accordance with certain principles of the invention.

In the focused dosimetry device as described below, and in the various embodiments of the components thereof, a substance, such as medicinal cream, compound, or the like, is deposited into a barrel of a cartridge of the device. The volume of the cream deposited in the cartridge represents multiple doses of the cream, wherein several single doses can be administered successively therefrom over a period of time. The components of the multiple dose device can be disassembled, cleaned, stored and/or transported, if desired or necessary, during periods when the device is not being used.

The consistency of the cream is such that the cream does not flow easily within or out of the cartridge without a force being applied to the barrel-confined mass thereof. Typically then, a plunger head or plunger within the barrel is urged by pushing a stem through a proximal end of the barrel, with a distal end of the stem in contact with the head or plunger, to force the cream to exit the barrel at the distal end thereof.

The focused dosimetry device described below, and the various embodiments of the components thereof, is particularly useful for applying and focusing each administered dose of cream to affected areas of vaginal and anal openings of the human anatomy. The device, or portions thereof, may be useful for other purposes without departing from the spirit and scope of the invention.

The below-described focused dosimetry device includes a dispensing end at which the cream is dispensed from the barrel of the cartridge to the affected area of the patient. Such dispensing end of the focused dosimetry device will hereinafter be referred to as the distal end. The opposite end of the device, which includes a stem, will be referred to as the proximal end of the device. The end of any component of the focused dosimetry device, which is closest to the distal end of the device, will be referred to as the distal end of the component, and the other end of such component, which is opposite the distal end, will be referred to as the proximal end.

Referring to FIGS. 1 and 2, a focused dosimetry device 560 is typically used in multiple dose applications. The device 560 includes a cartridge 562, having a barrel 564, for containing a substance such as the medicinal cream, or any other substance having a cream-like consistency. The device 560 is a multiple dose device, but could be used in a single dose application.

In the device 560, the barrel 564 is formed with a hollow interior barrel passage 566, having a distal opening 568 at a distal end thereof and a proximal opening 570 at proximal end thereof. A flange 572 is formed radially outward on the barrel 564 at the proximal end thereof. The device 560 further includes a plunger 608, which is located within the hollow barrel passage 566, and a stem 610, which is insertable into the proximal opening 570 to facilitate movement of the plunger within the barrel passage toward the distal opening 568 thereof, to dispense cream from within the barrel passage externally at the distal end of the cartridge 562. The device 560 also includes a carrier 612, which supports the cartridge 562 and the stem during use of the device, and, in conjunction with the flange 572 of the barrel 564, facilitates the dispensing of successive single dose applications of the cream from the barrel 564.

A small-diameter sleeve 574 forms an integral part of the cartridge 562, and is in axial alignment with the barrel 564 at the distal end thereof, and forms a sleeve passage 576, which is in communication with the barrel passage 566. The exterior of the small-diameter sleeve 574 is tapered in the form of a frustum, with the smaller diameter of the frustum located at the distal end of the sleeve, and the axis of the frustum being coincidental with the axis of the barrel 564.

A large-diameter sleeve 578 also forms an integral part of the cartridge 562, at the distal end thereof, and is in axial alignment with the barrel 564, and coaxial alignment with the small-diameter sleeve 574. An internal cylindrical wall of the large-diameter sleeve 578 can be threaded or unthreaded, and the proximal end of the sleeve is closed and not in communication with the barrel passage 566.

An applicator 580, or tip, has a body 581, which is formed with an axial entry passage 582 therein, and which is assembled with the cartridge 562 at the distal end of the barrel 564, for example, by use of a known coupling facility such as the coupling facility identified with U.S. registered trademark LUER-LOK.

Figure 34:
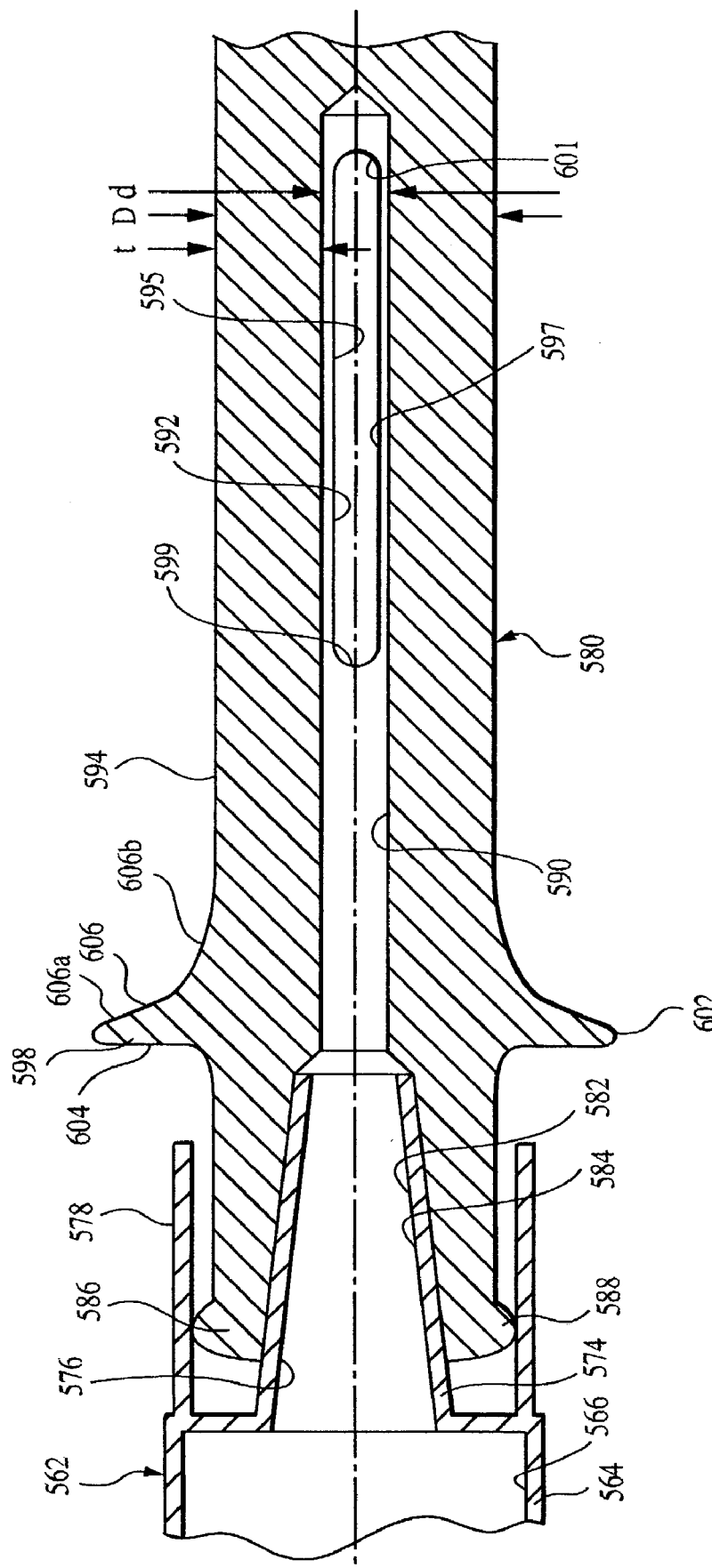
FIG. 34 is an enlarged partial sectional view showing a proximal end of the applicator of FIG. 1 in assembly with a distal end of the cartridge of FIG. 1, and showing the configuration of a first embodiment of an elongated slot of the applicator of FIG. 1 in relation to an axial delivery passage of the applicator, in accordance with certain principles of the invention.

In particular, as shown in FIG. 34, the axial entry passage 582 of the applicator 580 is formed with a tapered wall 584 which tapers axially inward from the proximal end of the passage to the distal end thereof, and which mates with the exterior taper of the sleeve 574 of the cartridge 562 to facilitate one aspect of the attachment of the applicator with the cartridge. The axial entry passage 582 extends from a proximal end of the body 581 toward a distal end of the body and to a distal end of the axial entry passage. The body 581 of the applicator 580 is formed with a first ear 586 and a second ear 588, which extend in radially opposite directions from the proximal end of the applicator. Upon assembly of the applicator 580 with the cartridge 562, the outboard ends of the ears 586 and 588 are threadedly, or frictionally, applied to, and within, the large-diameter sleeve 578 by rotation of the applicator. The rotation of the applicator 580 also enhances the tapered assembly of the tapered small-diameter sleeve 574 with the tapered proximal opening 584 of the axial entry passage 582.

It is noted that facilities, other than as described above, can be used to attach the applicator 580 to the cartridge 562 without departing from the spirit and scope of the invention. Such attachment facilities could be threaded, unthreaded, tapered, press fit, or the like.

As further shown in FIGS. 1 and 34, the applicator 580 is also formed with an inner axial delivery passage 590, which extends axially of the body 581, with a uniform diameter "d", between an open proximal end and a closed distal end of the axial delivery passage. The axial entry passage 582 is in communication with the axial delivery passage 590, with the distal end of the axial entry passage and the proximal end of the axial delivery passage being located at a transaxial juncture of the passages. The uniform diameter "d" of the axial delivery passage is less than a prescribed diameter of the axial entry passage 582 at the transaxial juncture.

The axial entry passage 582 could be formed in a configuration other than the tapered wall 584 without departing from the spirit and scope of the invention. Further, the prescribed diameter of the axial entry passage 582 could be measured at any transaxial location of the body 581 between the proximal end and the distal end of the axial entry passage without departing from the spirit and scope of the invention. The uniform diameter "d" of the axial delivery passage 590 is less than the prescribed diameter of the axial entry passage 582 regardless of the transaxial location at which the measurement of the prescribed diameter is taken.

A pair of diametrically-opposed, axially extending, elongated slots 592 are formed in the body 581. Each of the slots 592 are in communication with, and extend radially through the body 581 from, the axial delivery passage 590 and exit to a smooth exterior surface 594 of the body. As shown in FIG. 34, each of the slots 592 is formed with axially-extending, interfacing side walls 595 and 597 which extend from a proximal end 599 of the slot to a distal end 601 thereof, and define the width of the slot. The axial entry passage 582, the axial delivery passage 590, and the slots 592 are all in communication with each other to facilitate the smooth flow of the cream from the barrel 564 and through the applicator 580 to a location externally of the applicator.

Figure 35:
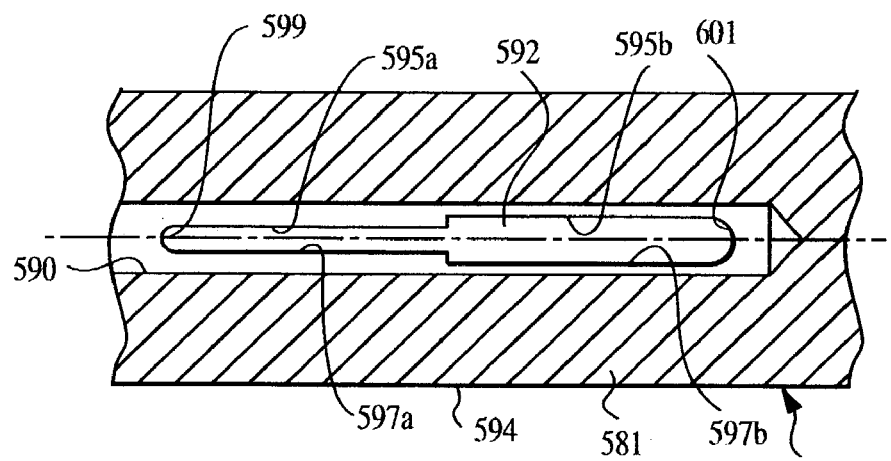
FIG. 35 is an enlarged partial sectional view showing the configuration of a second embodiment of the elongated slot of the applicator of FIG. 1 in relation to the axial delivery passage of the applicator, in accordance with certain principles of the invention.

Referring to FIG. 34, in a first embodiment of the slots 592, the interfacing side walls 595 and 597 of each of the slots are uniformly spaced from each other between the proximal end 599 of the slot and the distal end 601 thereof. Referring to FIG. 35, in a second embodiment of the slots 592, interfacing side walls 595a and 597a of each slot are uniformly separated by a prescribed distance from the proximal end 599 of the slot to an intermediate location between the proximal end and the distal end 601. Interfacing side walls 595b and 597b of each of the slots 592 are uniformly spaced from each other by a distance greater than the prescribed distance from the intermediate location to the distal end 601 of the slot.

Figure 36:
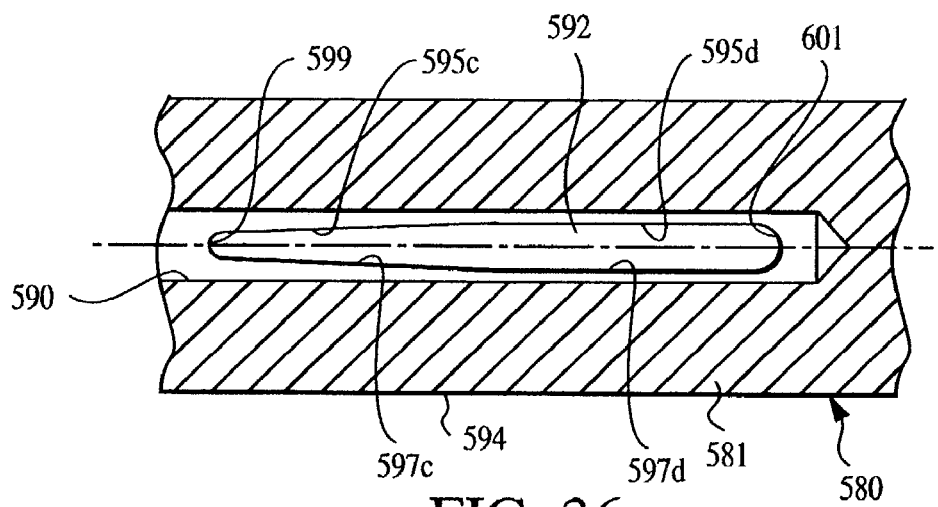
FIG. 36 is an enlarged partial sectional view showing the configuration of a third embodiment of the elongated slot of the applicator of FIG. 1 in relation to the axial delivery passage of the applicator, in accordance with certain principles of the invention.

Referring to FIG. 36, in a third embodiment of the slots 592, interfacing side walls 595c and 597c of each slot are separated by a first prescribed distance at the proximal end 599 of the slot. The interfacing side walls 595c and 597c of each of the slots 592 diverge from each other between the proximal end 599 of the slot to an intermediate location between the proximal end 599 of the slot and the distal end 601 thereof at which the side walls are spaced apart by a second prescribed distance greater than the first prescribed distance. Interfacing side walls 595d and 597d of each of the slots 592 are uniformly spaced from each other by a distance equal to the second prescribed distance from the intermediate location to the distal end 601 of the slot.

Figure 37:
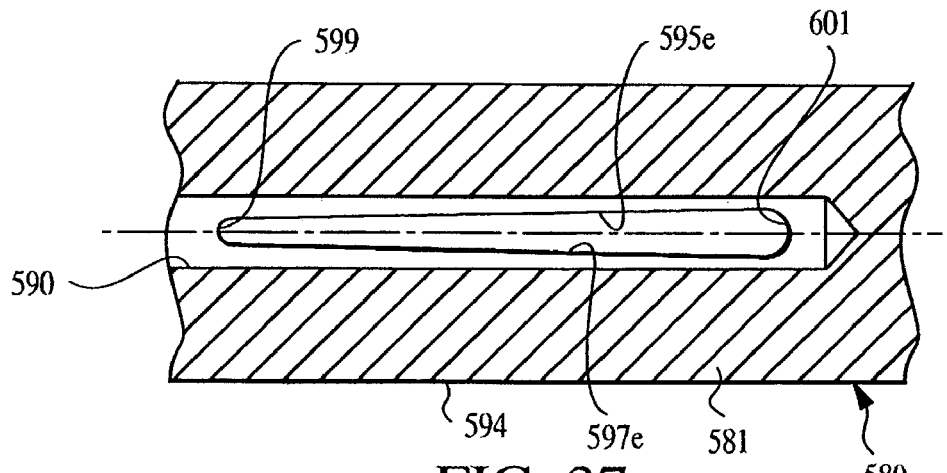
FIG. 37 is an enlarged partial sectional view showing the configuration of a fourth embodiment of the elongated slot of the applicator of FIG. 1 in relation to the axial delivery passage of the applicator, in accordance with certain principles of the invention.

Referring to FIG. 37, interfacing side walls 595e and 597e of each of the slots 592 are spaced from each other by a first prescribed distance at the proximal end 599 of the slot, and the interfacing side walls diverge from each other between the proximal end of the slot to the distal end 601 thereof at which the side walls are spaced apart by a second prescribed distance which is greater than the first prescribed distance.

As shown in FIG. 34, the body 581 of the applicator 580 is formed with an external diameter "D", while the axial delivery passage 590 is formed with the diameter "d". Further, the body 581 is formed with a thickness "t" between an interior wall of the axial delivery passage 590 and the exterior surface 594 of the body. The thickness "t" of the body 581 of the applicator 580 is greater than the diameter "d" of the axial delivery passage 590. Further, the diameter "d" of the axial delivery passage 590 is approximately twenty-five percent of the external diameter "D" of the body 581. With the applicator 580 having the axial delivery passage 590 with a relatively small diameter, in comparison to the thickness and diameter of the body 581, comparatively less cream will remain within the applicator following the delivery of each dose.

Referring to FIG. 34, the applicator 580 is formed with a tactile-indicating flange 598 near the proximal end thereof. The applicator body 581 is formed with the smooth exterior surface 594 of a uniform external diameter from the flange 598 nearly to the distal end of the body, and is interrupted only by the openings of the slots 592 formed in the exterior surface. The flange 598 extends radially outward from the exterior surface 594 of the body 581 to an outer edge surface 602 of the flange. The flange 598 is formed with a proximal surface 604 facing in a direction toward the proximal end of the body 581 and a distal surface 606 facing in a direction toward the distal end of the body. The distal surface 606 of the flange 598 is formed by a straight portion 606a which extends from the outer edge surface 602 of the flange, radially inward toward the axis of the body 581 and toward the distal end of the body, to an inboard edge of the straight portion spaced radially outward from the external surface of the body. The distal surface 606 of the flange 598 is formed with a concave portion 606b which extends from the inboard edge of the straight portion 606a toward the distal end, and to the external surface 594, of the body 581. The flange 598, with the concave portion 606b and the angled flat portion 606a, provides a user-friendly tactile indication to the patient that the applicator 580 has been inserted into the vaginal or anal cavity at the appropriate distance for placement of the slots 592 adjacent the areas to be treated with the cream.

Figure 5:
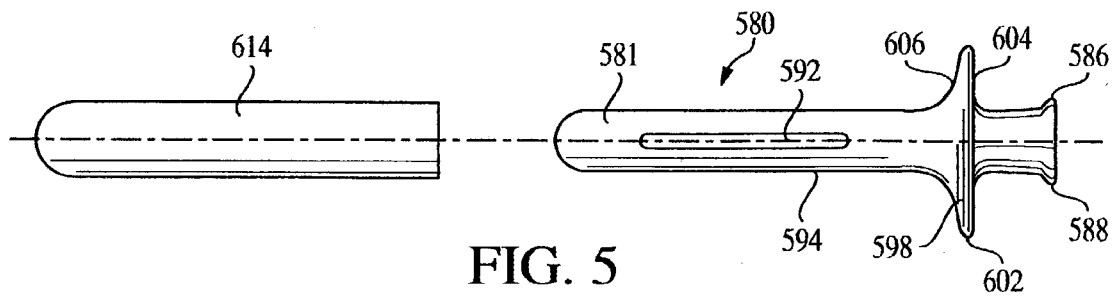
FIG. 5 is a side view showing the applicator of FIG. 1, with a cover for the applicator, in accordance with certain principles of the invention.

After a single dose of the cream has been dispensed from the focused dosimetry device 560, the applicator 580 may remain in assembly with the distal end of the cartridge 562. Referring to FIG. 5, if the applicator 580 is to remain in assembly with the cartridge 562, a sleeve-like cover 614, which is open at a proximal end and closed at a distal end thereof, is slipped over the body 581 of the applicator 580 to cover the slots 592, thereby preventing unwanted release of the cream from the applicator during periods when the device is not in use.

Figure 6:
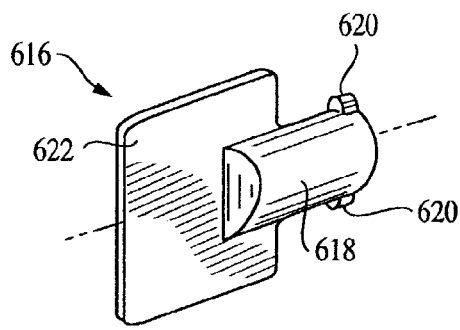
FIG. 6 is a perspective view showing a cap for assembly with the cartridge of FIG. 1.

During periods when the device 560 is not being used, the applicator 580 can be removed from assembly with the cartridge 562. A cap 616, as shown in FIG. 6, can be attached in place of the applicator 580 to seal the distal opening 568 of the barrel 64 to prevent cream from discharging or leaking undesirably from the barrel. The cap 616 is formed with a cylindrical cup 618, which is formed with a tapered opening for receipt of the tapered small-diameter sleeve 574 when assembling the cap with the cartridge 562. A pair of ears 620 are formed radially outward at the proximal end of the cup 618. A flat vane 622 is formed integrally with a closed end of the cup 618 to facilitate handling of the cap 616 during assembly and disassembly of the cap with respect to the sleeve 574.

Referring to FIGS. 1, 28, 29, 32 and 33, a first embodiment of a plunger for use with the focused dosimetry device 560 is identified as the plunger 608, and is formed from a compliant or elastomeric material such as, for example, butyl rubber or buna rubber. The plunger 608 is formed with a slight axial point on a distal surface thereof which is facing toward the distal end of the barrel 564, and fits snugly within the interior walls of the passage 566 of the barrel 564 to provide a moving seal between portions of the barrel passage on opposite sides of the plunger. The plunger 608 is formed with a proximal surface 624 in which an axial recess is formed, and has a prescribed axial length.

Figure 28:
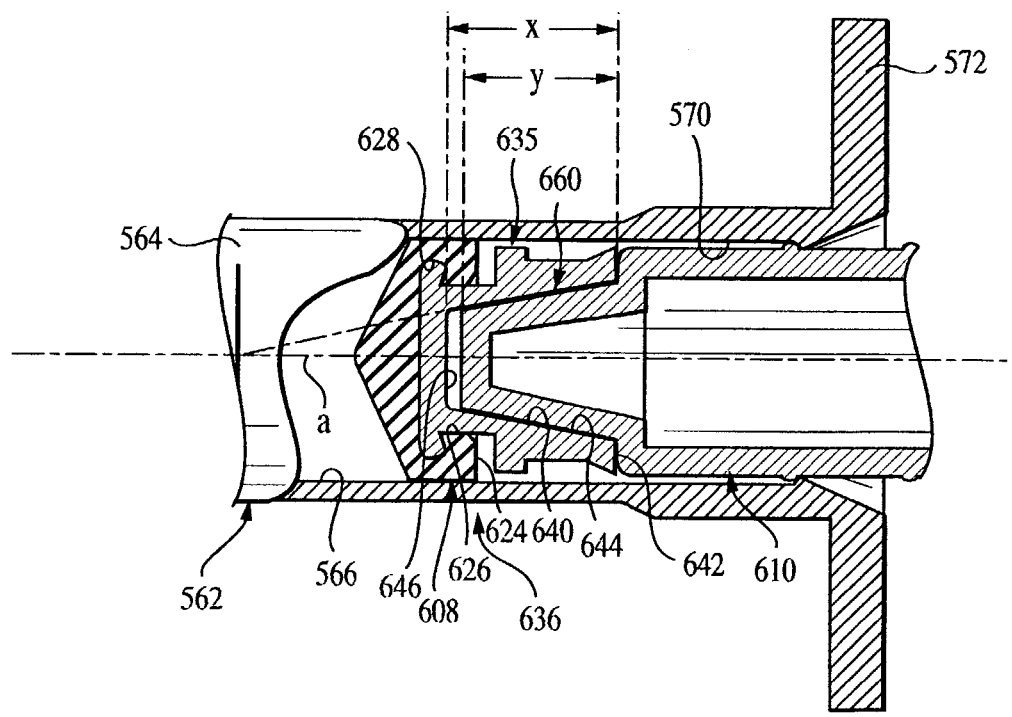
FIG. 28 is a sectional view showing a first embodiment of an interfacing arrangement of a proximal end of a plunger and a distal end of the stem, with a receptor section therebetween, in accordance with certain principles of the invention.

Referring to FIG. 28, the axial recess of the plunger 608 is formed axially in a prescribed shape which includes an opening 626 of a first diameter, in communication with a comparatively larger cavity 628 of a second diameter, formed farther axially within the plunger toward the distal end thereof, where the second diameter is greater than the first diameter.

Figure 30:
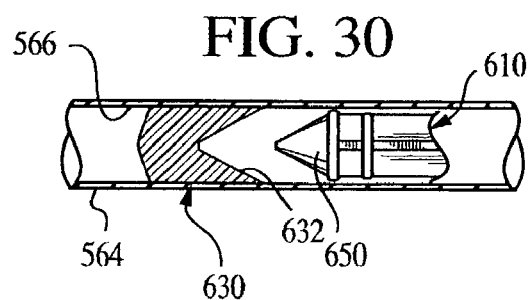
FIG. 30 is a sectional view showing a third embodiment of an interfacing arrangement of the proximal end of the plunger and the distal end of the stem within the cartridge of FIG. 1, in accordance with certain principles of the invention.

As shown in FIG. 30, a plunger 630, which is representative of a second embodiment for use with the focused dosimetry device 560, is formed from the compliant material and with a slight axial point on a distal surface thereof, which is facing toward the distal end of the barrel 564. The plunger 630 has an axial length which is greater than the prescribed length of the plunger 608. A proximal surface 632 of the plunger 630 is formed about the axis of the barrel 564 in the shape of a conical recess.

Figure 31:
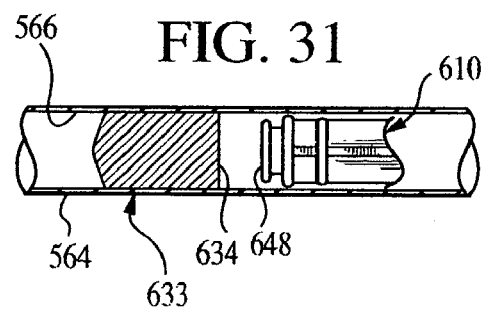
FIG. 31 is a sectional view showing a fourth embodiment of an interfacing arrangement of the proximal end of the plunger and the distal end of the stem within the cartridge of FIG. 1, in accordance with certain principles of the invention.

Referring to FIG. 31, a plunger 633, which is representative of a third embodiment for use with the focused dosimetry device 560, is formed from the compliant material and with a slight axial point on a distal surface thereof, which is facing toward the distal end of the barrel 564. A proximal surface 634 of the plunger 633 is flat, is perpendicular to the axis of the barrel 564, and has an axial length greater than the prescribed length of the plunger 608.

As shown in FIG. 28, a receptor section 635 is assembled with the plunger 608 to form a plunger head 636, and is composed of a thermoplastic material such as, for example, acetal, and is rigid in comparison to the compliant plunger 608. The receptor section 635 is formed with a structure 638 which is complementary with the hollow structure of the combined profile of the opening 626 and the cavity 628 formed in the proximal end of the plunger 608 to facilitate coupling assembly of the receptor section with the plunger to form the plunger head 636. A receptor opening 640 is formed in a proximal end 642 of the receptor section 635 and is formed with a prescribed configuration. In particular, the receptor opening 640 is formed with a tapered side wall 644 at a taper angle "a" and at a depth of "x" to a floor 646 of the receptor opening.

In accordance with certain principles of this invention, various embodiments of a stem are described and illustrated. Each of the various embodiments of the stem includes a distal end, a proximal end and an intermediate section which extends between the distal and proximal ends thereof. In further accordance with certain principles of this invention, various embodiments of the distal end of the stem are described and illustrated, various embodiments of the proximal end are described and illustrated, and various embodiments of the intermediate section are described and illustrated. Each of the various embodiments of the distal end, the proximal end and the intermediate section are interchangeable with each other to provide the a plurality of embodiments of the stem. For the purposes description, each of the embodiments of the stem will be identified, and referred to, as the stem 610.

Figure 29:
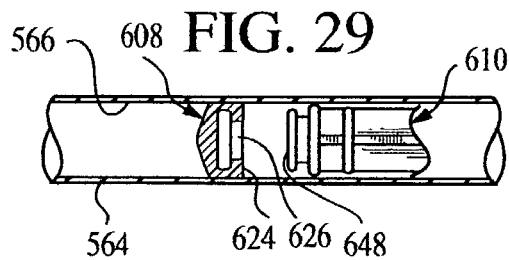
FIG. 29 is a sectional view showing a second embodiment of an interfacing arrangement of the proximal end of the plunger and the distal end of the stem within the cartridge of FIG. 1, in accordance with certain principles of the invention.

As shown in FIGS. 1, 29, 31, 32 and 33, in a first embodiment of a distal end of the stem 610, the stem is formed with a distal surface 648 which is flat and perpendicular to the axis of the barrel 564. Referring to FIGS. 1, 29 and 31, the distal surface 648 of the stem 610 interfaces with the proximal surface 624 of the plunger 608, and engages the proximal surface when the stem is moved toward the distal end of the barrel 564 to push the plunger toward the distal end of the barrel and discharge the cream therefrom.

As shown in FIG. 30, in a second embodiment of the distal end of the stem 610, the distal end is formed as a cone 650, which is complementary in shape to the conically shaped proximal surface 632 of the plunger 630. The cone 650 interfaces with the proximal surface 632 of the plunger 610, and engages the proximal surface when the stem 610 is pushed toward the distal end of the barrel to facilitate the discharge of the cream from the distal end of the barrel.

Figure 32:
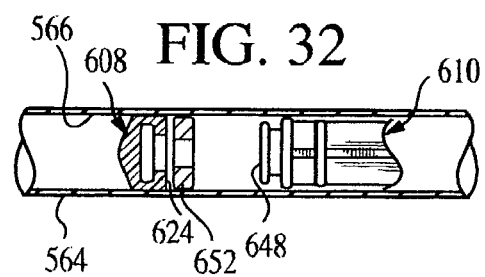
FIG. 32 is a sectional view showing a fifth embodiment of an interfacing arrangement of the proximal end of the plunger and the distal end of the stem within the cartridge of FIG. 1, in accordance with certain principles of the invention.
Figure 33:
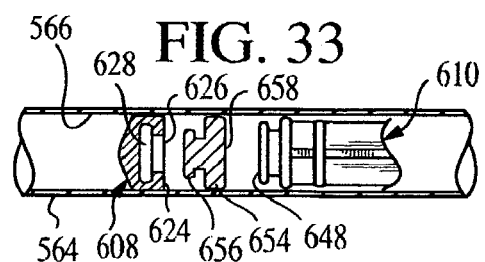
FIG. 33 is a sectional view showing a sixth embodiment of an interfacing arrangement of the proximal end of the plunger and the distal end of the stem within the cartridge of FIG. 1, in accordance with certain principles of the invention.

Referring to FIG. 32, a floating insert 652 is located within the passage 566 of the barrel 564 between the proximal surface 624 of the plunger 608 and the distal surface 648 of the stem 610. The insert 652 is formed with a first face positioned for engagement with the proximal surface 624 of the plunger 608, and a second face positioned for engagement with the distal surface 648 of the stem 610. In similar fashion, as shown in FIG. 33, an insert 654 is formed with a projection 656 which extends in a distal direction from the insert, and which is formed in a shape complementary to the prescribed shape of the axial recess of the plunger 608 for receipt of the projection within the recess. The insert 654 is formed with a face 658 positioned for engagement with the distal surface 648 of the stem 610.

As shown in FIG. 28, in a third embodiment of the stem 610, the distal end of the stem is formed with a stem structure 660 in a configuration similar to the prescribed configuration of the receptor opening 640, the only difference being that the stem structure extends for a distance "y" from the stem member, which is less than the depth "x" of the receptor opening. Because of the difference in the depth "x" and the distance "y," the distal end of the stem structure 660 does not engage the floor 646 of the receptor opening 640 when the stem structure is assembled fully within the receptor opening, as shown in FIG. 28. This allows the stem structure 660 to fully seat within the receptor opening 640 without interfering engagement between the floor 646 of the receptor opening and the distal end of the stem structure.

When the stem structure 660 is being assembled with the plunger head 636, the matching taper of the stem structure and the receptor opening 640 facilitates a piloting engagement thereof. During this process, the stem structure 660 and the receptor opening 640 cooperate quickly to locate the optimum interfacing engagement thereof in preparation for the application of a force to the stem 610 to move the plunger head 636 toward the distal end of the barrel 564.

When engaging surfaces of two objects having the same taper are moved axially together, the angle of such taper plays a part in the manner in which the surfaces interface with each other. Based, to some extent, on the materials of the two objects in the area of the interfacing surfaces, there is a critical angle of taper below which the interfacing surfaces engage with a taper-lock interference fit. In order to release the two objects from such an interference fit, considerable force must be used to pull the objects apart, which tends to disturb the location of both objects. If the taper is above the critical angle, the interfacing surfaces do not engage in a taper-lock interference fit, and a first of the objects can be moved easily away from a second of the objects without disturbing the location of the second object.

The critical taper angle consideration is important in the operation of the multiple dose device 560 which includes the plunger head 636 and the receptor section 635, because, in multiple dose situations, the stem 610 is removed from assembly with the plunger head 636 following the application of each dose. It is important that the plunger head 636 remain in its end-of-dose position after each dose is administered so that the plunger head will be in the appropriate position for the initiation of the next dose to be administered. If there had been a taper-lock interference fit between the stem structure 660 and the wall of the receptor opening 640, considerable force would have been required to separate the stem structure from within the receptor opening, which would have resulted in undesirable movement of the plunger head 636. This is particularly so with respect to the device 560, because there is no way to grasp and hold steady the plunger head 636 while removing the stem 610. Also, the plunger head 636 is, in essence, floating in a lubricated environment provided by the cream contained within the barrel 564, which would tend to ease and enhance the undesirable movement of the plunger head when the stem 610 is being removed.

Based on the above described structure of the device 560, the prescribed configuration of the taper angle "a" is structured to create a piloted engagement of the stem structure 660 within the receptor opening 640 and to preclude a taper-lock interference fit.

Figure 11:
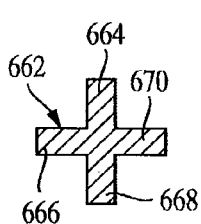
FIG. 11 is a sectional view taken along line 11—11 of FIG. 10 showing a plus-sign cross sectional form of the first embodiment of the intermediate section of the stem of FIG. 10, in accordance with certain principles of the invention.

As shown in FIGS. 1, 2, 10 and 11, in a first embodiment of an intermediate section of the stem 610, an intermediate section 662 is formed with four rails or splines 664, 666, 668 and 670 which extend between the distal and proximal ends of the stem, and are arranged so that the intermediate section has a prescribed cross section in the shape of a plus sign as shown in FIG. 11.

Figure 14:
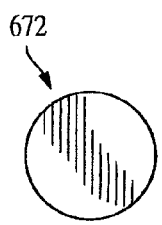
FIG. 14 is a sectional view taken along line 14—14 of FIG. 13 showing a solid round cross section of the second embodiment of the intermediate section of the stem of FIG. 13, in accordance with certain principles of the invention.
Figure 13:
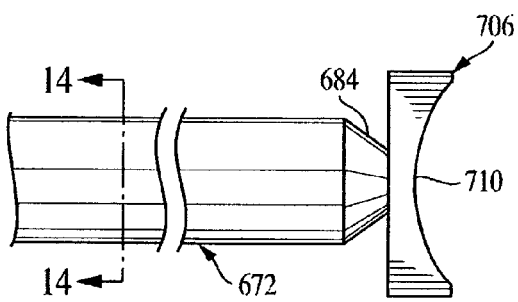
FIG. 13 is a side view showing a second embodiment of an intermediate section of the stem of FIG. 1, in accordance with certain principles of the invention.
Figure 15:
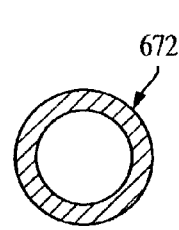
FIG. 15 is a sectional view showing a representation of a hollow round cross section of the second embodiment of the intermediate section of the stem of FIG. 13, in accordance with certain principles of the invention.

As shown in FIGS. 13, 14 and 15, in a second embodiment of an intermediate section of the stem 610, an intermediate section 672 is formed externally in a cylindrical configuration having a prescribed circular cross section which extends between the distal and proximal ends of the stem. The prescribed cross section of the intermediate section 672 can be a solid circular cross section (FIG. 14) or a hollow circular cross section (FIG. 15).

Figure 17:
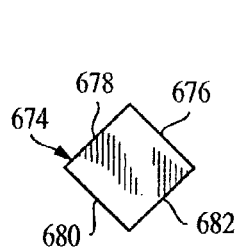
FIG. 17 is a sectional view taken along line 17—17 of FIG. 16 showing a solid diamond or square cross section of the third embodiment of the intermediate section of the stem of FIG. 16, in accordance with certain principles of the invention.
Figure 16:
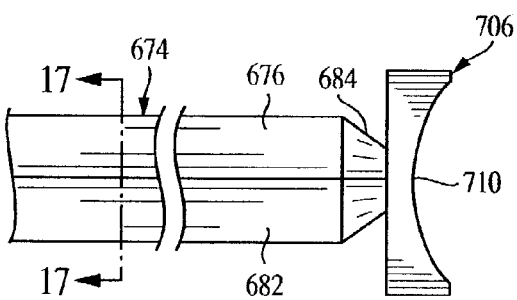
FIG. 16 is a side view showing a third embodiment of an intermediate section of the stem of FIG. 1, in accordance with certain principles of the invention.
Figure 18:
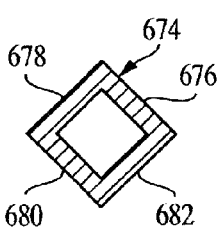
FIG. 18 is a sectional view showing a representation of a hollow diamond or square cross section of the third embodiment of the intermediate section of the stem of FIG. 16, in accordance with certain principles of the invention.

As shown in FIGS. 16, 17 and 18, in a third embodiment of an intermediate section of the stem 610, an intermediate section 674 is formed externally with multiple sides 676, 678, 680 and 682 which are arranged to form a prescribed cross section which is diamond shaped. The prescribed cross section of the intermediate section 674 can be a solid diamond cross section (FIG. 17) or a hollow diamond cross section (FIG. 18). It is noted that, depending on the longitudinal orientation of the intermediate section 674, the prescribed cross section could be considered as a square cross section, solid or hollow, without departing from the spirit and scope of the invention.

Figure 20:
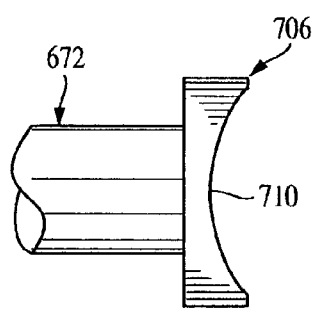
FIG. 20 is a partial side view showing a proximal end of the second embodiment of the intermediate section of the stem of FIG. 13 in flush engagement with a distal surface of the fourth embodiment of the thumb rest of FIG. 9, in accordance with certain principles of the invention.
Figure 19:
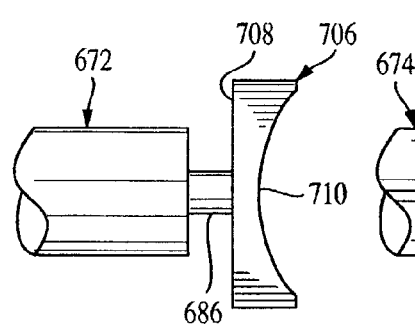
FIG. 19 is a partial side view showing a reduced or necked section between the intermediate section of the second embodiment of the stem of FIG. 13 and a distal surface of the fourth embodiment of the thumb rest of the stem of FIG. 9, in accordance with certain principles of the invention.
Figure 21:
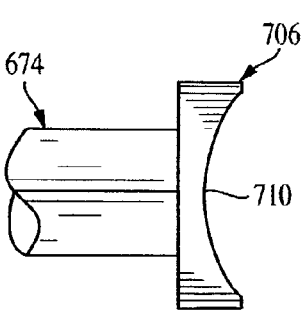
FIG. 21 is a partial side view showing a proximal end the third embodiment of the intermediate section of the stem of FIG. 16 in flush engagement with the distal surface of the fourth embodiment of the thumb rest of FIG. 9, in accordance with certain principles of the invention.

As shown in FIGS. 1, 2, 10, 13 and 16, a proximal end portion of the intermediate section of the stem 610 is formed with a tapered portion 684. As shown in FIG. 19, the distal end portion of the intermediate section of the stem 610 could be formed with fully reduced or necked portion 686, or, as shown in FIGS. 20 and 21, could be extended axially fully to the proximal end of the intermediate section.

Referring to FIGS. 1 and 2, a first embodiment of a thumb rest of the stem 610 for use with the focused dosimetry device 560 is identified as a thumb rest 688 having a distal surface 690, to which the proximal end of the intermediate section of the stem is attached. The thumb rest 688 is formed with a proximal portion 692, of a prescribed configuration, which, in the thumb rest 688, is a flat configuration as illustrated in FIG. 1.

Figures 7, 8:
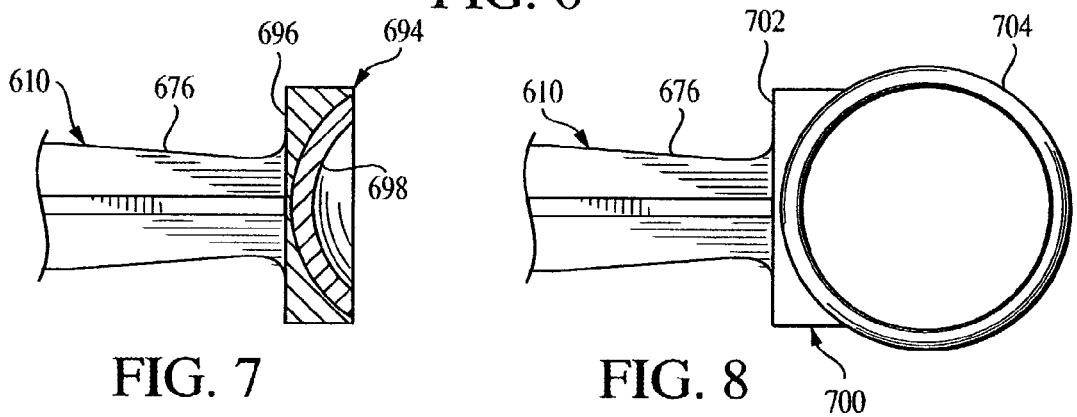
FIG. 7 is a partial sectional view showing a first embodiment of a thumb rest of the stem of FIG. 1, in accordance with certain principles of the invention.
FIG. 8 is a partial sectional view showing a second embodiment of a thumb rest of the stem FIG. 1, in accordance with certain principles of the invention.

Referring to FIG. 7, a second embodiment of a thumb rest of the stem 610 for use with the focused dosimetry device 560 is identified as a thumb rest 694 having a distal surface 696, to which the proximal end of the intermediate section of the stem is attached. The thumb rest 694 is formed with a proximal portion 698, of a prescribed configuration, which, in the thumb rest 688, is a dished configuration as illustrated in FIG. 7.

Referring to FIG. 8, a third embodiment of a thumb rest of the stem 610 for use with the focused dosimetry device 560 is identified as the thumb rest 700 having a distal surface 702, to which the proximal end of the intermediate section of the stem is attached. The thumb rest 700 is formed with a proximal portion 704, of a prescribed configuration, which, in the thumb rest 700, is a ring configuration as illustrated in FIG. 8.

Figure 9:
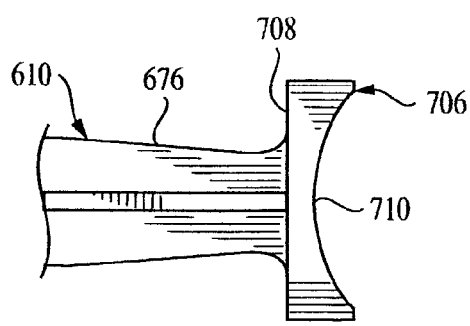
FIG. 9 is a partial sectional view showing a fourth embodiment of a thumb rest of the stem of FIG. 1, in accordance with certain principles of the invention.
Figure 12:
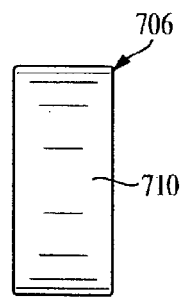
FIG. 12 is an end view showing a proximal surface of the fourth embodiment of the thumb rest of FIG. 9, in accordance with certain principles of the invention.

Referring to FIGS. 9, 10, 13, 16, 19, 20 and 21, a fourth embodiment of a thumb rest of the stem 610 for use with the focused dosimetry device 560 is identified as a thumb rest 706 having a distal surface 708, to which the proximal end of the intermediate section of the stem is attached. The thumb rest 706 is formed with a proximal portion 710, of a prescribed configuration, which, in the thumb rest 706, is a concave configuration as illustrated in FIGS. 9 and 12.

Figure 22:
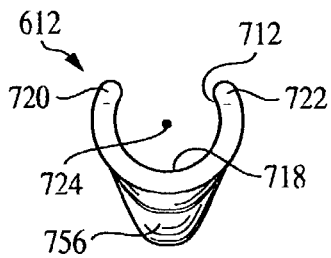
FIG. 22 is a left end view of the carrier of FIG. 4 showing a cartridge-receiving nest of the carrier, in accordance with certain principles of the invention.
Figure 27:
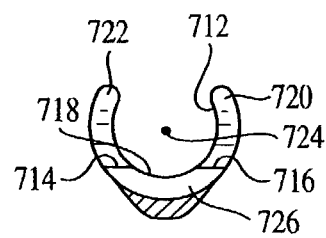
FIG. 27 is a sectional view taken along line 27—27 of FIG. 2, with the cartridge removed, showing a groove of the carrier of FIG. 4 for receiving a portion of the flange of the cartridge of FIG. 1, in accordance with certain principles of the invention.

Referring to FIGS. 1, 2, 3 and 4, the device 560 also includes the carrier 612, which is formed with a C-shaped cartridge-receiving nest 712, which receives the barrel 564 and is also referred to as the barrel-receiving nest. A pair of integrally joined, spaced shelves 714 and 716 extend axially from a proximal end of the C-shaped cartridge-receiving nest 712 toward a proximal end of the carrier 612, with a trough 718 (FIG. 4) extending between the shelves and from the nest. As shown in FIGS. 22 and 27, the C-shaped nest 712 is formed with end portions 720 and 722, which extend above an axis 724 of the cartridge 562 (FIG. 22). This facilitates reception of the barrel 564 of the cartridge 562 within the nest 712 by a snap fit to retain the cartridge with the carrier 612, and thereby provides a means for removably retaining the barrel 564 within the barrel-receiving nest 712.

The shelves 714 and 716, and the trough 718, extend in a proximal direction from the C-shaped nest 712, and are fully below the axis 724 of the cartridge 562 as viewed in FIG. 27. As particularly shown in FIG. 4, four axially-spaced grooves 726, 728, 730 and 732 are formed transaxially in the shelves 714 and 716, and the trough 718, and are formed with a width which will receive a portion 734 of the cartridge flange 572, as shown in FIG. 2.

Figure 4:
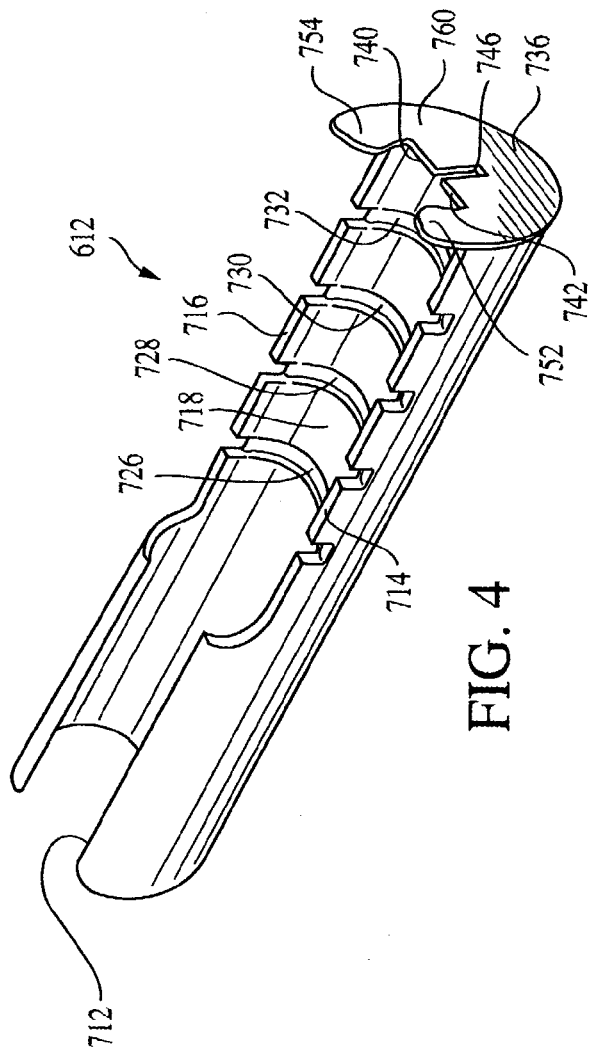
FIG. 4 is a perspective view showing the carrier of the of FIG. 1, in accordance with certain principles of the invention.
Figure 23:
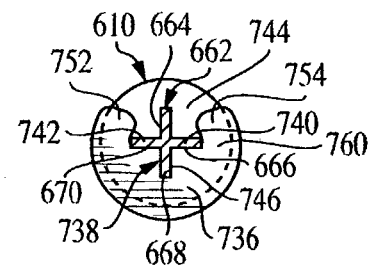
FIG. 23 is a sectional view taken along line 23—23 of FIG. 2 showing the first embodiment of the intermediate section of the stem of FIG. 10 mounted in a support member of the carrier of FIG. 4, in accordance with certain principles of the invention.

As shown in FIG. 4, the carrier 612 is formed integrally with a support member 736 at the proximal end of the carrier. The support member 736 can be formed alternately with any one of several different embodiments of a passage 738, each of which has a shape which conforms at least partially to a respective one of the several different embodiments of the prescribed cross section of the intermediate section of the stem 610. For example, the cross section of the intermediate section 662 of the stem 610 is the plus-sign cross section as illustrated in FIGS. 11 and 23. When the intermediate section 662 is used with device 560, the passage 738 of the support member 736 is formed with two spaced shelves 740 and 742, which are separated by a gap, and which are located in a common plane. The shelves 740 and 742 face an opening 744 formed in the support member 736. The passage 738 further includes a channel 746 formed in the support member 736, which extends from the gap between the shelves 740 and 742 in a direction away from the opening 744, and which is perpendicular to the given plane.

Referring to FIG. 23, when the intermediate section 662 of the stem 610 is assembled with the support member 736, the rails 666 and 670 of the intermediate section rest on the shelves 740 and 742, respectively, the rail 668 is located in the channel 746, and the rail 664 is located in the opening 744. The width of the channel 746 is slightly wider that the width of the rail 668, whereby the intermediate section 662 is allowed to move axially through the passage 738. In this manner, the support member 736 and the passage 738 formed through the support member provide a means for allowing the intermediate section 662 of the stem 610 to be moved along the axis of the stem relative to the support member.

Figure 25:
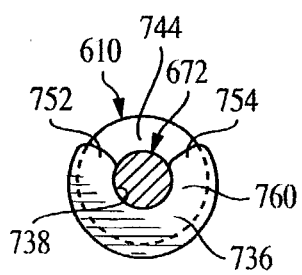
FIG. 25 is a sectional view showing the second embodiment of the intermediate section of the stem of FIG. 13 mounted in the support member of the carrier of FIG. 4, in accordance with certain principles of the invention.
Figure 26:
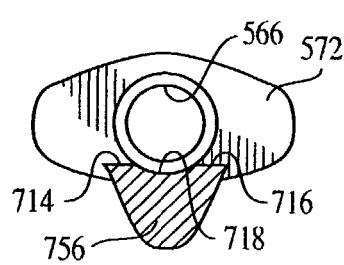
FIG. 26 is a sectional view taken along line 26—26 of FIG. 2 showing the cartridge of FIG. 1 located in the cartridge-receiving nest of the carrier of FIG. 22, in accordance with certain principles of the invention.

Referring to FIG. 25, the cross section of the intermediate section 672 of the stem 610 is the circular cross section as illustrated in FIGS. 14 and 15. When the intermediate section 672 is used with device 560, the passage 738 of the support member 736 is formed in a partial circular configuration, the diameter of which is slightly larger than the diameter of the intermediate section 672. The passage 738 faces the opening 744.

Referring further to FIG. 25, when the intermediate section 672 of the stem 610 is assembled with the support member 736, the slightly larger diameter of the passage 738 allows the intermediate section to move axially through the passage. In this manner, the support member 736 and the passage 738 formed through the support member provide a means for allowing the intermediate section 672 of the stem 610 to be moved along the axis of the stem relative to the support member 736.

Figure 24:
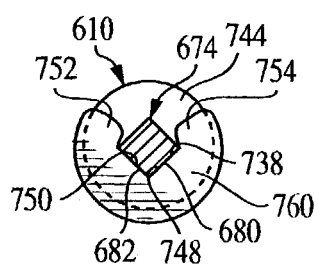
FIG. 24 is a sectional view showing the third embodiment of the intermediate section of the stem of FIG. 16 mounted in the support member of the carrier of FIG. 4, in accordance with certain principles of the invention.

Referring to FIG. 24, the cross section of the intermediate section 674 of the stem 610 is the diamond cross section, or square cross section, as illustrated in FIGS. 17 and 18. When the intermediate section 674 is used with the device 560, the passage 738 of the support member 736 is formed in a partial diamond or square configuration, in the form of two adjoining walls 748 and 750 which are configured in a "V" shape. The passage 738, including the walls 748 and 750, faces the opening 744.

Referring again to FIG. 24, when the intermediate section 674 of the stem 610 is assembled with the support member 736, the sides 680 and 682 of the intermediate section seat on the walls 748 and 750, respectively. The "V" shaped spacing of the walls 748 and 750 of the passage 738 is slightly greater than the "V" shaped spacing of the sides 680 and 682 of the intermediate section 674 to allow the intermediate section to move axially through the passage. In this manner, the support member 736 and the passage 738 formed through the support member provide a means for allowing the intermediate section 674 of the stem 610 to be moved along the axis of the stem relative to the support member 736.

Referring to FIGS. 23, 24 and 25, the support member 736 is formed with a pair of spaced ears 752 and 754 located at opposite sides of the opening 744, and are normally spaced apart by a distance which defines a normal width of the opening. The ears 752 and 754 are sufficiently resilient to be spread farther apart by a distance greater than the normal width of the opening 744 to facilitate movement of the intermediate section 662, 672 or 674 of the stem 610 through the opening and into, or out of, the passage 738. The resilient ears 752 and 754 are formed with portions which return to the normal width condition, when the intermediate section has been located in the passage 738, and engage an adjacent portion of the intermediate section 662, 672 or 674 to maintain the intermediate section within the passage. In this manner, the support member 736, the passage 738, the opening 744 and the resilient ears 752 and 754 provide a means for removably retaining the stem 610 with the carrier 612. Further, the pair of ears 752 and 754, and the resiliency thereof, provide a means for biasingly engaging the intermediate section 662, 672 or 674 of the stem 610 to maintain the intermediate section of the stem within the passage 738.

Referring to FIGS. 4, 23, 24 and 25, the support member 736 of the carrier 612 is formed with a stop surface 760, which is in the path of the distal surface 690, 696, 702 or 708 of the thumb rest 688, 694, 700 or 706, respectively. When the stem 610 is moved toward the distal end of the barrel 564 to dispense the cream from the barrel, the distal surface 690, 696, 702 or 706 of the stem functions as a surface which will engage the stop surface 760 to preclude further, and thereby limit, movement of the stem 610 toward the distal end of the barrel 564.

Referring to FIGS. 2, 3, 21 and 26, a plurality of spaced ridges 756 are formed transversely of the axis, and on a first side, of the carrier 612, opposite a second side of the carrier which includes the cartridge-receiving nest. The plurality of ridges 756 are spaced apart to form a plurality of spaced grooves 758 on the first side of the carrier 612. During use of the focused dosimetry device 560, the user may place the user's fingers in the grooves 758 to properly locate the fingers when the stem 610 is to be depressed by the user's thumb. In this manner, the grooves 758 provide a means formed on the carrier 612 for facilitating the locating of the fingers of the user on the carrier during use of the device 560.

The use of the device 560, by one administering the single, given doses of the medicated cream, will be described below with respect to one embodiment of the stem 610 which includes the distal end 648, the intermediate section 662 and the thumb rest 706. It is to be understood that the elements of all of the above-described embodiments of each of the distal ends 648 and 650 of the stem 610, the intermediate sections 662, 672 and 674 of the stem, the thumb rests 688, 694, 700 and 706 of the stem, the plungers 608, 630 and 633, the inserts 652 and 654, and the receptor section 660, can be used in all possible permuted combinations with the cartridge 562 and the carrier 612 in the manner described below without departing from the spirit and scope of the invention.

When preparing the device 560 for use, the plunger 608 is inserted into the barrel 564 so that the distal end of the plunger is facing toward the distal end of the barrel. A measured supply of the medicated cream is deposited into the barrel 564 through the distal end thereof, and thereby engages and urges the plunger 608 toward the proximal end of the barrel. With respect to the device 560, the measured supply of the medicated cream will be sufficient for the dispensing of four successive single doses of the cream from the distal end of the barrel 564. With the measured supply of the medicated cream having been deposited into the barrel 564, the plunger 608 has been moved within the barrel and located at a first-dose starting position within the barrel.

The applicator 580 is then attached to the distal end of the barrel 564, as described above. If desired, the distal end of the stem 610 may be assembled within the passage 566 of the barrel, from the proximal end of the barrel. As an alternative, the stem 610 may be assembled with the barrel 564 at a later stage as described below. In either instance, when the stem 610 is assembled within the barrel 564, the distal end of the stem is moved into engagement with the proximal end of the plunger 608 which, as noted above, is in the first-dose starting position, ready for the dispensing of a first dose of a given amount of the cream. In this arrangement, and for the purpose of description, the stem 610 is now considered to be in a dose-delivery start position.

It is noted that, with respect to the embodiment of the plunger head 636 as illustrated in FIG. 28, the stem structure 660 at the distal end of the stem 610 will engage the receptor section 635 in the manner described above, rather than the distal end of the stem directly engaging the plunger 608. Otherwise, the cream-dispensing movement of the stem 610 into engagement with the receptor section 635 will result in dispensing movement of the plunger 608 in the same manner as described above.

Thereafter, the flange 572 is aligned with the first groove 726 of the carrier 612, which is the closest of the grooves 726, 728, 730 and 732 to the distal end of the shelves 714 and 716. The cartridge 562 is then snapped into the C-shaped nest 712, whereby the portion 734 of the flange 572 is moved into the groove 726. If the stem 610 has not been assembled previously with the cartridge 612, the proximal end of the stem can now be assembled within the barrel 564 in the manner described below.

If the stem 610 has been assembled with the barrel 564 before assembly of the barrel within the C-shaped nest 712, the intermediate section 662 of the stem will be assembled within the passage 738 of the carrier support member 736 at the same time that the barrel is assembled in the C-shaped nest and the portion 734 of the flange 572 is inserted into the groove 726.

If the stem 610 has not been assembled with the barrel 564 before assembly of the barrel within the C-shaped nest 712, the intermediate section 662 of the stem can now be assembled independently with the carrier 612 by moving the intermediate section 662 through the opening 744 between the resilient ears 752 and 754 and laterally into the passage 738. With the independent assembly of the intermediate section 662, care must be taken to insure that the distal end of the stem 610 is sufficiently located, prior to assembly of the stem with the carrier, to clear the proximal end of the previously assembled barrel 564 as the intermediate section is moved laterally into the passage 738. After the intermediate section 662 has been independently assembled within the passage 738, the stem 610 can be moved axially within the passage to locate the distal end of the stem within the proximal end of the barrel, and in engagement with the proximal end of the plunger 608 at the dose-delivery start position of the stem.

As noted above, the stem 610 may be assembled with the carrier 612 prior to the assembly of the cartridge 562 with the carrier. This is accomplished by moving the intermediate section 662 through the opening 744 between the resilient ears 752 and 754, and laterally into the passage 738. The stem 610 is then retracted in a proximal direction to insure that the distal end of the stem will not interfere with the subsequent assembly of the cartridge 562 within the C-shaped nest 712 of the carrier 612. After the cartridge 562 has been assembled within the C-shaped nest 712, the stem 610 is moved axially within the passage toward the distal end of the carrier 612 to insert the distal end of the stem into the proximal end of the barrel 654 and into engagement with the proximal end of the plunger 608 at the first-dose start position.

With the stem 610 having been located at the dose-delivery start position, the distal surface 708 of the thumb rest 706 of the stem is spaced by a prescribed stem-travel distance from the stop surface 760 of the support member 736 of the carrier 612. The prescribed stem-travel distance is equal to the distance of travel of the stem 610, and thereby the plunger 608, necessary to facilitate the dispensing of the single or given dose of the cream from the distal end of the barrel 564. The prescribed stem-travel distance is also equal to the distance between each adjacent pair of the grooves 726, 728, 730 and 732 of the carrier 612.

The device 560 is now ready for use by the patient, who typically will self-administer the given dose of medicated cream. The patient grasps the device 560 and places the fingers of the administering hand around the device, with the fingers coming to rest in the grooves 758 and the thumb placed on the proximal potion 710 of the thumb rest 706. The applicator 580 is placed in the vaginal or anal cavity and, in response to the tactile sensing of engagement with the distal surface 606 of the flange 598, the patient depresses the thumb rest 706 to move the distal end of the stem 610 toward the distal end of the barrel 564. The thumb rest 706 is thereby moved from the dose-delivery start position toward the stop surface 760 of the support member 736, whereby the medicated cream is being dispensed and applied to the target site of the patient.

Eventually, the distal surface 708 of the thumb rest 706 engages the stop surface 760, whereby the stem 610 is precluded from moving any farther. The plunger 608 has now moved to a first-dose completion position associated with the completion of the dispensing of the first or given dose of the medicated cream. The first-dose completion now represents a second-dose starting position for the plunger 608 in anticipation of the subsequent dispensing of a second dose of the medicated cream.

Figure 10:
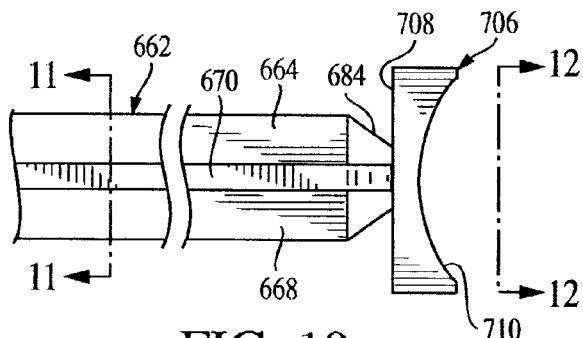
FIG. 10 is a side view showing a first embodiment of an intermediate section of the stem of FIG. 1, in accordance with certain principles of the invention.

The assembly of the cartridge 562 and the stem 610 is now extracted from assembly with the carrier 612, whereby the barrel 564 is removed from the C-shaped nest 712, and the stem is removed through the opening 744 from the passage 738 of the support member 736. The stem 610 is then removed from assembly with the barrel 564, whereby the plunger 608 remains within the barrel in the second-dose start position. The applicator 580 can be removed from assembly with the barrel 564 and cleaned if desired. The cap 616 is then assembled with the distal end of the barrel 564. The applicator 580, the capped cartridge 562, the stem 610 and the carrier 612 can then be stored until preparation for the dispensing of the second dose of the cream begins. As shown in FIGS. 1, 2 and 10, the tapered portion 684 of the intermediate section 662 facilitates a reduction of the cross sectional area of the stem 610 which is to be passed through the opening 744 of the support member 736, and thereby provides for a relatively easy removal of the stem from assembly within the passage 738 of the support member. Also, instead of being tapered, the proximal end of the intermediate section 662 could be formed with the necked portion 686, as represented in FIG. 19, to facilitate easy removal of the stem from assembly with the carrier 612.

As an alternative to the above-described dismantling procedure, with the barrel 564 and the stem 610 in assembly with the carrier 612 after the dispensing of the first dose of the cream, the stem can be withdrawn from the barrel but remain assembled with the carrier. The cartridge 562 can then be removed from the C-shaped nest 712 independently of the stem 610. The distal end 648 of the stem 610 is then moved axially within the passage 738 toward the distal end of the carrier 612, and is retained with the carrier during storage thereof. As represented in FIGS. 20 and 21, the radially outboard surface of the intermediate section 662 (FIG. 10) can be uniform, i.e., not tapered, and extends into flush engagement with the distal surface 708 of the finger rest 706 to insure that the stem 610 can not be easily removed without some urging of the intermediate section 662 through the opening 744.

Also, with reference to FIG. 5, if the applicator 580 is to be retained with the distal end of the barrel 564 while the cartridge 562 is stored, the cover 614 is slipped over the body 581 during a storage period to seal the slots 592.

In preparation for the dispensing of the second dose of the medicated cream, assuming that the cartridge 562 and the stem 610 had been disassembled from the carrier 612 following the dispensing of the first dose, the patient re-assembles the distal end of the stem within the barrel 564 and into engagement with the proximal end of the plunger 608. As noted above, as the dispensing of the first dose was completed, the plunger 608 had been moved to the second-dose start position, and has been retained and remains at this position during storage and handling of the cartridge 562 following the dispensing of the first dose.

The flange 572 of the barrel 564 is then located in alignment with the groove 728 of the carrier 612, which is the second closest of the grooves 726, 728, 730 and 732 to the distal end of the shelves 714 and 716. As the cartridge 562 is assembled within the C-shaped nest 712, the portion 734 of the flange 572 is inserted into the groove 728, and the intermediate section 662 of the stem 610 is assembled within the passage 738. In effect then, the flange 572 has been moved in a proximal direction from the first groove 726, which is the position of the flange during dispensing of the first dose of the cream, to the second groove 728, which is the position of the flange during the dispensing of the second dose, by a distance equal to the prescribed stem-travel distance. With the movement of the flange 572 from the first groove 726 to the second groove 728, the stem 610 is effectively moved the same distance, with respect to the carrier 612, i.e., by a distance equal to the prescribed stem-travel distance. Therefore, the distal surface 708 of the thumb rest 706 of the stem 610 is again located at the dose-delivery start position of the stem.

The patient then grasps the device 560 in the manner described above, with the fingers in the grooves 758 and the thumb on the thumb rest 706. The applicator 580 is placed in the vaginal or anal cavity in the manner described above, and the patient depresses the thumb rest 706 to move the stem 610 from the dose-delivery start position toward the distal end of the cartridge 562. Movement of the stem 610 in this manner results in movement of the plunger 608 from the second-dose start position toward the distal end of the cartridge 562 whereby the second dose of the given amount of the medicated cream is being dispensed from the barrel 564, through the applicator and onto the areas of the patient to be treated.

Eventually, the distal surface 708 of the thumb rest 706 engages the stop surface 760 of the support member 736 to preclude any further movement of the stem 610 and the plunger 608. The dispensing of the second dose of the given amount of the medicated cream is now complete. At this juncture, the plunger 608 is now located at a third-dose start position within the barrel 564, and is in position for the beginning of the subsequent dispensing of the third dose of the given amount of the cream.

The cartridge 562 and the stem 610 are removed from assembly with the carrier 612 as described above with respect to the completion of the dispensing of the first dose of the given amount of the cream. As noted above, the stem 610 may be retained with the carrier 612 for storage. The disassembled elements of the device 560 can now be cleaned and stored, awaiting the preparation for the dispensing of the third dose of the given amount of the cream.

In preparation for the dispensing of the third dose of the given amount of the cream, the elements of the device 560 are re-assembled as described above. The flange 572 of the barrel 564 is aligned with the groove 730 of the carrier 612, which is the third closest groove of the grooves 726, 728, 730 and 732 to the distal end of the shelves 714 and 716. The stem 610 and the cartridge 562 are assembled with the carrier 612 as described above, whereby the stem is again in the dose-delivery start position. The thumb rest 706 is depressed whereby the stem 610 is moved to move the plunger 608 to dispense the third dose of the given amount of the cream. The plunger 608 is now in a fourth-dose start position.

Following the dispensing of the third dose of the given amount of the cream, the elements of the device 560 are dissembled and stored, and are subsequently re-assembled for dispensing of a fourth dose of the given amount of the cream. In preparation for the dispensing of the fourth dose, the flange 572 is aligned with, and the portion 734 is inserted into, the groove 532, which is the farthest of the grooves 526, 528, 530 and 532 from the distal end of the shelves 714 and 716. With the plunger 608 in the fourth-dose starting position, and the stem 610 in the dose-delivery start position, the stem is moved to dispense the fourth dose of the given amount of the medicated cream.

While the above-described embodiment of the focused dosimetry device 560 included the carrier 612 with the four grooves 726, 728, 730 and 732, carriers having more, or less, grooves of this type could be used for dispensing one or more doses of a substance such as, for example, the medicated cream, without departing from the spirit and scope of the invention. Further, a carrier having multiple grooves such as, for example, the carrier 612 could be used to dispense a single dose of a substance without departing from the spirit and scope of the invention. For example, with respect to the carrier 612, an amount of cream sufficient for a single dose application could be deposited into the barrel 564, and move the plunger 608 within the barrel for a distance associated with the single dose. With a one-dose volume of the cream in the barrel 564, the plunger 608 would be located at a start position which is physically the same as the fourth-dose start position as described above. The patient would align the flange 572 of the cartridge 562 with the groove 732, which is the farthest of the grooves 726, 728, 730 and 732 from the distal end of the shelves 714 and 716. When the portion 734 of the flange 732 is inserted into the groove 732, the stem 610 is placed in the dose-delivery start position. The stem 610 can then be moved to begin dispensing the single dose of the cream. When the distal surface 708 engages the stop surface 760, the dispensing of the single dose of the cream is completed.

With the focused dosimetry device 560, the stem 610, the carrier 612 and the applicator 580 could be retained for re-use, while prepackaged cartridges 562 having single or multiple doses could be obtained as needed, and discarded when emptied. Also, the cover 614 and the cap 616 could be retained for re-use.

It is noted that, while the above-described various embodiments of the device 560 have included the applicator 580, other applicators of this type could be used with any of the various embodiments of the device.

Figure 38:
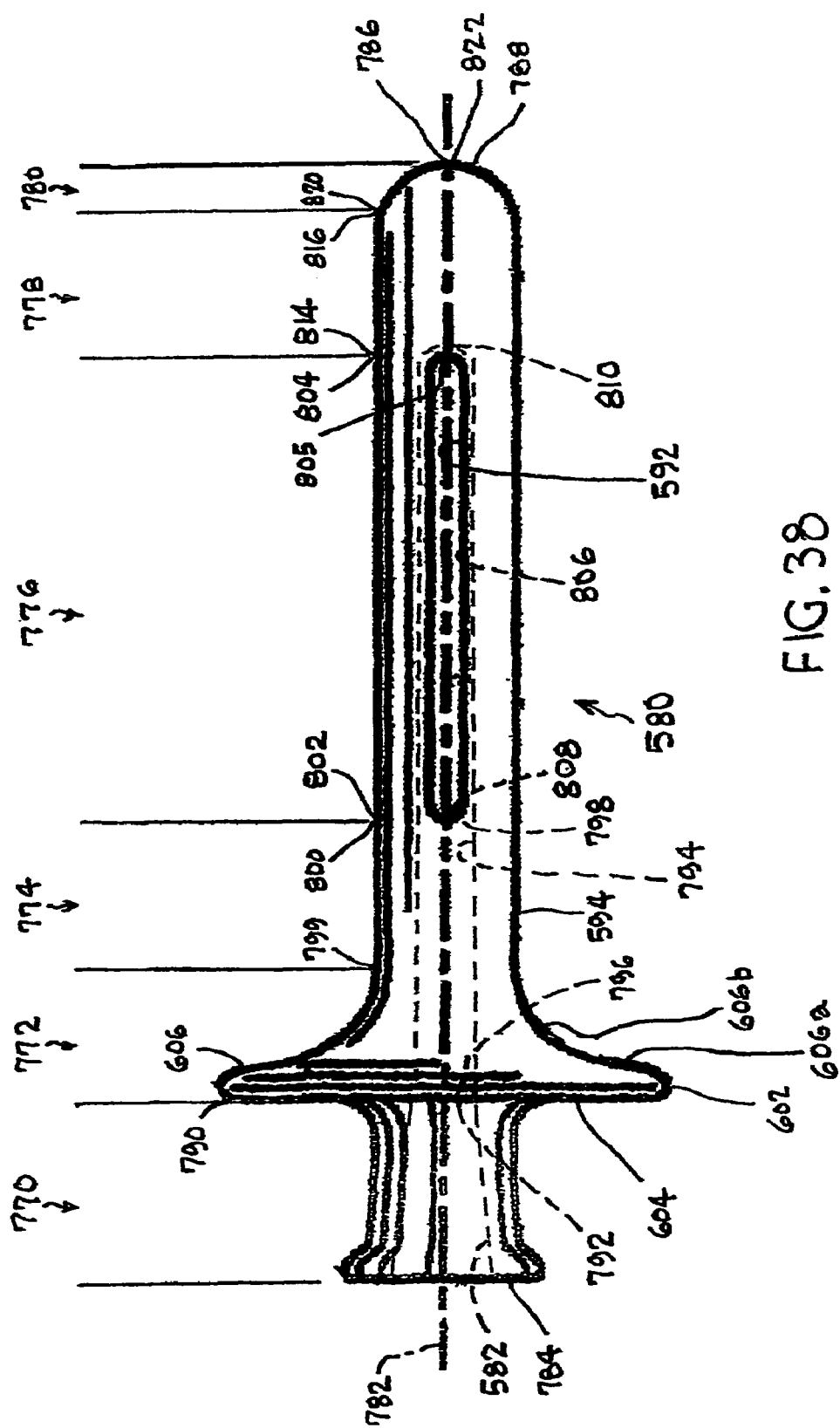
FIG. 38 is a side view showing an applicator having integrally-joined sections in accordance with certain principles of the invention.

Referring to FIG. 38, and in an alternative manner of describing the applicator 580, which is also shown in FIGS. 1, 5 and 34, the applicator includes the unitary body 581, formed by six integrally-joined sections, identified as a proximal section 770, a flange section 772, a passage section 774, a slot section 776, a solid section 778, and a dome section 780. As noted above, the applicator 580 is designed to facilitate the dispensing of a medicinal substance therethrough, where the medicinal substance has a cream-like consistency of the type which does not flow without a force being applied thereto.

The body 581 of the applicator 580 is formed about an axis 782, which extends from a proximal end 784 of the body to an exterior axial surface 786 of a closed distal end 788 of the body. The proximal section 770 of the body 581 extends from the proximal end 784 of the body toward the closed distal end 788 of the body, and to a distal end 790 of the proximal section.

The proximal section 770 of the body 581 is formed with the axial entry passage 582, which extends from the proximal end 784 of the body toward the closed distal end 788 of the body, and to a distal end 792 of the axial entry passage. The axial entry passage 582 is formed with a prescribed diameter, at least at the proximal end 784 of the body.

The body 581 is also formed with an axial intermediate passage 794 having a proximal end 796, which is coincidental with the distal end 792 of the axial entry passage 582. The axial intermediate passage 794 is formed with a uniform passage diameter, which is less than the prescribed diameter, and extends toward the closed distal end 788 of the body 581, and to a distal end 798 of the axial intermediate passage.

The body 581 is formed about the axis 782 thereof with the passage section 774, which has a uniform exterior diameter. The passage section 774 extends from a proximal end 799 thereof toward the closed distal end 788 of the body, and to a distal end 800 of the passage section, and fully surrounds at least a portion of the axial intermediate passage 794 to the distal end 798 thereof.

The body 581 is formed about the axis 782 thereof with the slot section 776, which has the uniform exterior diameter. The slot section 776 extends from a proximal end 802 thereof toward the closed distal end 788 of the body 581, and to a distal end 804 of the slot section, with the proximal end 802 of the slot section formed integrally with the distal end 798 of the passage section 774.

A slot delivery passage 806 is formed axially through the slot section 776 of the body 581 from a proximal end 808 of the slot delivery passage toward the closed distal end 788 of the body, and to a closed distal end 810 of the slot delivery passage, with the proximal end 808 of the slot delivery passage being in communication with the distal end 798 of the axial intermediate passage 794.

The at least one axially-elongated slot 592 is formed radially through the slot section 776 of the body 581 in unobstructed radial communication with the slot delivery passage 806 and an exterior of the body, and extends from the proximal end 802 of the slot section toward the closed distal end 788 of the body, and to a distal end 805 of the at least one axially-elongated slot. The slot delivery passage 806 is formed with the uniform passage diameter, interrupted only by the presence of the at least one axially-elongated slot 592.

The body 581 is formed with the solid section 778, having the uniform exterior diameter, which extends from a closed proximal end 814 of the solid section toward the closed distal end 788 of the body, and to a closed distal end 816 of the solid section. The closed proximal end 814 of the solid section 778 is formed integrally with the distal end 804 of the slot section 776.

The body 581 is formed with the dome section 780 in the form of a solid dome 780, which extends from a closed proximal end 820 of the dome section to a closed distal end 822 thereof, which is coincidental with the exterior axial surface 786 of the closed distal end 788 of the body 581. The closed proximal end 820 of the dome section 780 is formed integrally with the closed distal end 816 of the solid section 778. The solid section 778 and the dome section 780 are exclusive of any opening.

It is noted that the axial intermediate passage 794 of the passage section 774, and the slot delivery passage 806 of the slot section 776, are axially aligned and combine to form the axial delivery passage 590 as illustrated in FIG. 34. Further, as described above, and with reference to FIG. 38, the axially aligned axial intermediate passage 794 and the slot delivery passage 806 are formed with the uniform passage diameter. This uniform passage diameter is consistent with the uniform diameter "d" of the axial delivery passage 590 as described above with respect to FIGS. 1 and 34.

As further shown in FIG. 38, the flange 598 is located in the flange section 772, between the proximal section 770 and the passage section 774. The flange 598 is integrally joined with adjacent portions of the body 581, at opposite axial ends thereof, and fully radially surrounds a portion of the axial intermediate passage 794. Thus, except for the presence of the at least one axially-elongated slot 592, successive portions of the body 581, which are located in the three sections identified as the flange section 772, the passage section 774 and the slot section 776, surround the axial delivery passage 590 (FIG. 34), which, as noted above, is formed by the axial intermediate passage 794 and the slot delivery passage 806 illustrated in FIG. 38.

Referring to FIG. 38, the flange 598 extends radially outward from an exterior surface 594 of the body 581 to an outer edge surface 602 of the flange. The flange 598 is formed with a proximal surface 604 facing in a direction toward the proximal end 784 of the body 581 and a distal surface 606 facing in a direction toward the closed distal end 788 of the body. The distal surface 606 of the flange 598 is formed by a straight portion 606a which extends from the outer edge surface 602 of the flange, radially inward toward the axis 782 of the body 581 and toward the closed distal end 788 of the body, to an inboard edge of the straight portion spaced radially outward from the external surface of the body. The distal surface 606 of the flange 598 is further formed with a concave portion 606b which extends from the inboard edge of the straight portion 606a toward the closed distal end 788 of the body 581, and to the external surface 594 of the body.

Thus, with the structure of the body 581 as described above, there is full communication from an exterior of the body 581, at the proximal end 784 thereof, through the axial entry passage 582, the axial intermediate passage 794, the slot delivery passage 806, the at least one axially-elongated slot 592, and an exterior of the body adjacent the at least one axially-elongated slot.

In general, the above-identified embodiments are not to be construed as limiting the breadth of the present invention. Modifications, and other alternative constructions, will be apparent which are within the spirit and scope of the invention as defined in the appended claims.

What is claimed is:

1. An applicator for dispensing a medicinal substance therethrough, where the substance has a cream-like consistency of the type which does not flow easily without a force being applied thereto, which comprises:

a body having an external surface, formed about an axis which extends from a proximal end of the body to an exterior axial surface of a closed distal end of the body;

the body formed with a proximal section which extends from the proximal end of the body toward the closed distal end of the body, and to a distal end of the proximal section;

the proximal section of the body formed with an axial entry passage extending through the proximal section from the proximal end of the body toward the closed distal end of the body, and to a distal end of the axial entry passage;

the axial entry passage being formed with a prescribed diameter at the proximal end of the body;

the body being formed with an axial intermediate passage having a proximal end in communication with the distal end of the axial entry passage, and extending toward the closed distal end of the body, and to a distal end of the axial intermediate passage; the axial intermediate passage being formed with a uniform passage diameter which is less than the prescribed diameter;

the body being formed about the axis thereof with a passage section, having a uniform exterior diameter, which extends from a proximal end thereof toward the closed distal end of the body, and to a distal end of the passage section;

the body formed with a flange section having a proximal end formed integrally with the distal end of the proximal section, and a distal end formed integrally with the proximal end of the passage section of the body;

a flange located in the flange section of the body and extending radially outward from the external surface of the body to an outer edge surface of the flange;

the passage section of the body fully surrounding at least a portion of the axial intermediate passage to the distal end of the axial intermediate passage;

the body being formed about the axis thereof with a slot section, having the uniform exterior diameter, which extends from a proximal end of the slot section toward the closed distal end of the body, and to a distal end of the slot section, with the proximal end thereof being formed integrally with the distal end of the passage section;

a slot delivery passage formed axially through the slot section of the body from a proximal end thereof toward the closed distal end of the body, and to a closed distal end of the slot delivery passage, with the proximal end of the slot delivery passage being in communication with the distal end of the axial intermediate passage;

at least one axially-elongated slot formed radially through the slot section of the body in unobstructed communication with the slot delivery passage and an exterior of the body, and extending from the proximal end of the slot section toward the distal end of the slot section, and to a distal end of each of the at least one axially-elongated slot;

the slot delivery passage being formed with the uniform passage diameter interrupted only by the presence of the at least one axially-elongated slot;

the body formed with a solid section, having the uniform exterior diameter, which extends from a closed proximal end of the solid section toward the closed distal end of the body, and to a closed distal end of the solid section, with the closed proximal end of the solid section being formed integrally with the distal end of the slot section;

the body formed with a dome section in the form of a solid dome, which extends from a closed proximal end of the dome section to a closed distal end of the dome section, which is coincidental with the exterior axial surface of the closed distal end of the body;

the closed proximal end of the dome section being formed integrally with the closed distal end of the solid section; and the solid section and the dome section being exclusive of any opening.

2. The applicator as set forth in claim 1, which further comprises:

the at least one axially-elongated slot formed with interfacing side walls which are uniformly spaced from each other between a proximal end and the distal end of the at least one elongated slot.

3. The applicator as set forth in claim 1, which further comprises:

the at least one axially-elongated slot formed with interfacing side walls which are uniformly spaced from each other by a prescribed distance from a proximal end of the at least one axially-elongated slot to an intermediate location between the proximal end and the distal end thereof; and the interfacing side walls being uniformly separated by a distance greater than the prescribed distance from the intermediate location to the distal end of the at least one elongated slot.

4. The applicator as set forth in claim 1, which further comprises:

the at least one axially-elongated slot formed with interfacing side walls which are separated by a first prescribed distance at a proximal end of the at least one axially-elongated slot;

the interfacing side walls diverging from each other between the proximal end of the at least one axially-elongated slot to an intermediate location between the proximal end and the distal end thereof at which the side walls are spaced apart by a second prescribed distance greater than the first prescribed distance; and the interfacing side walls being uniformly separated by a distance equal to the second prescribed distance from the intermediate location to the distal end of the at least one axially-elongated slot.

5. The applicator as set forth in claim 1, which further comprises:

the at least one axially-elongated slot formed with interfacing side walls which are separated by a first prescribed distance at a proximal end of the at least one axially-elongated slot; and the interfacing side walls diverging from each other between the proximal end of the at least one axially-elongated slot to the distal end thereof at which the side walls are spaced apart by a second prescribed distance greater than the first prescribed distance.

6. The applicator for as set forth in claim 1, which further comprises:

the body formed with an exterior surface;

the axial intermediate passage and the slot delivery passage forming an axial delivery passage in, and extending along an axis of, the body;

the axial delivery passage formed with an interior wall having a uniform diameter "d";

the body formed with a thickness "t" between the interior wall of the axial delivery passage and the exterior surface of the body;

the thickness "t" of the body being greater than the diameter "d" of the axial delivery passage; and the axial delivery passage formed with a proximal end, through which the substance is introduced into the axial delivery passage, to a closed axial distal end of the axial delivery passage.

7. The applicator as set forth in claim 1, which further comprises:

the body formed with an external diameter "D";

the axial intermediate passage and the slot delivery passage combining to form an axial delivery passage in, and extending along an axis of, the body;

the axial delivery passage formed with a diameter "d" between axially spaced portions of the axial delivery passage;

the diameter "d" of the axial delivery passage being equal to approximately twenty-five percent of the external diameter "D" of the body; and the axial delivery passage formed with a proximal end, through which the substance is introduced into the axial delivery passage, and a closed distal end.

8. The applicator as set forth in claim 1, which further comprises:

the flange having a proximal surface facing in a direction toward the proximal end of the body and a distal surface facing in a direction toward the closed distal end of the body;

the distal surface of the flange formed by a straight portion which extends from the outer edge of the flange, radially inward toward the axis of the body and toward the closed distal end of the body, to an inboard edge of the straight portion spaced radially outward from the external surface of the body; and the distal surface of the flange formed with a concave portion which extends from the inboard edge of the straight portion toward the distal end, and to the external surface, of the body.

9. The applicator as set forth in claim 1, which further comprises:

a proximal end and the distal end of the at least one axially-elongated slot being located in a first plane and a second plane, respectively, which are parallel and spaced apart by an axial length of the at least one axially-elongated slot, and which extend radially from the axis of the body, to limit dispensing of the medicinal substance to an axially radial direction between the proximal end and the distal end of the at least one axially-elongated slot, from the slot delivery passage, and through the at least one axially-elongated slot.

10. The applicator as set forth in claim 1, which further comprises:

the slot section of the body being formed with an axial length which is greater than an axial length of the solid section of the body.

* * * * *